United States Patent [19]

Collins

[11] 4,275,201

[45] Jun. 23, 1981

[54] ARYL SUBSTITUTED DIKETONES

[75] Inventor: Joseph C. Collins, East Greenbush, N.Y.

[73] Assignee: Sterling Drug Inc., New York, N.Y.

[21] Appl. No.: 12,206

[22] Filed: Feb. 14, 1979

Related U.S. Application Data

[60] Division of Ser. No. 885,353, Mar. 13, 1978, Pat. No. 4,189,500, which is a division of Ser. No. 740,358, Nov. 10, 1976, Pat. No. 4,093,736, which is a continuation-in-part of Ser. No. 545,486, Jan. 30, 1975, Pat. No. 4,171,378, which is a continuation-in-part of Ser. No. 436,611, Jan. 25, 1974, Pat. No. 3,917,718, which is a continuation-in-part of Ser. No. 265,333, Jun. 22, 1972, Pat. No. 3,829,475.

[30] Foreign Application Priority Data

Jun. 18, 1973 [GB] United Kingdom ............... 28793/73

[51] Int. Cl.$^3$ ........................................... C07D 265/30

[52] U.S. Cl. ..................................... 544/171; 560/51; 560/73; 560/254; 424/248.55; 424/308; 424/321; 424/324; 564/88; 564/218; 564/221; 564/305

[58] Field of Search .......................... 560/51, 73, 254; 260/556 AR, 562, 568, 577; 424/248.55, 308, 321, 324

[56] References Cited

U.S. PATENT DOCUMENTS

| | | | |
|---|---|---|---|
| 2,641,608 | 6/1953 | Cusic | 560/51 |
| 3,956,374 | 5/1976 | Shepard | 560/51 |

*Primary Examiner*—Paul J. Killos
*Attorney, Agent, or Firm*—Thomas L. Johnson; B. Woodrow Wyatt

[57] ABSTRACT

Aryl substituted diketones and keto-esters, useful as antiviral agents and insecticides, are prepared by reacting an arylalkyl or arylalkenyl iodide with a metal salt of the appropriate diketone or keto-ester.

26 Claims, No Drawings

ARYL SUBSTITUTED DIKETONES

This application is a division of copending application Ser. No. 885,353, filed Mar. 13, 1978, now U.S. Pat. No. 4,189,500, which is in turn a division of application Ser. No. 740,358, filed Nov. 10, 1976, now U.S. Pat. No. 4,093,736, which in turn is a continuation-in-part of copending application Ser. No. 545,486, filed Jan. 30, 1975, now U.S. Pat. No. 4,171,378, which in turn is a continuation-in-part of copending application Ser. No. 436,611, filed Jan. 25, 1974, now U.S. Pat. No. 3,917,718, which in turn is a continuation-in-part of application Ser. No. 265,333, filed June 22, 1972, now U.S. Pat. No. 3,829,475.

This application relates to aryl substituted diketones and keto-esters, to the preparation thereof and to certain novel intermediates.

The compounds of the invention are of the structural formula

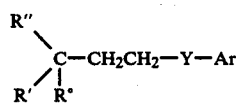

wherein
Y is selected from the group consisting of:

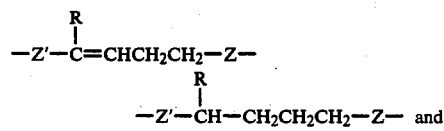

$$-Z'-C(R)=CHCH=CH-Z-;$$

R' is lower-alkanoyl of 2 to 6 carbon atoms;
R'' is lower-alkanoyl of 2 to 6 carbon atoms or carbo-lower-alkoxy of 2 to 6 carbon atoms;
R° is hydrogen, lower-alkyl of 1 to 4 carbon atoms or chloro;
R is hydrogen or lower-alkyl of 1 to 4 carbon atoms;
Z is a single bond, vinylene (only when the remainder of Y is unsaturated) or ethylene (only when Y is saturated);
Z' is a single bond, methylene or ethylene; and
Ar is phenyl, naphthyl or phenyl substituted by 3,4-methylenedioxy or from one to three monovalent substituents selected from the group consisting of lower-alkyl of 1 to 4 carbon atoms, lower-alkoxy of 1 to 4 carbon atoms, carbo-lower-alkoxy of 2 to 4 carbon atoms, halogen, nitro, trifluoromethyl, trifluoromethoxy, hydroxy, acyloxy of 1 to 10 carbon atoms, benzyloxy, alkanoylamino of 1 to 4 carbon atoms, dialkylamino where alkyl has from 1 to 4 carbon atoms, and aminosulfonyl.

The carbon chains of R, R', R'', R° and Ar substituents can be straight or branched, although primary or secondary alkyl moieties are preferred.

When two or three monovalent substituents are present on the phenyl ring of Ar, they can be the same or different.

The compounds of the invention where Z and Z' are both single bonds and R° is hydrogen are prepared as described in the following Reaction Sequences A and B.

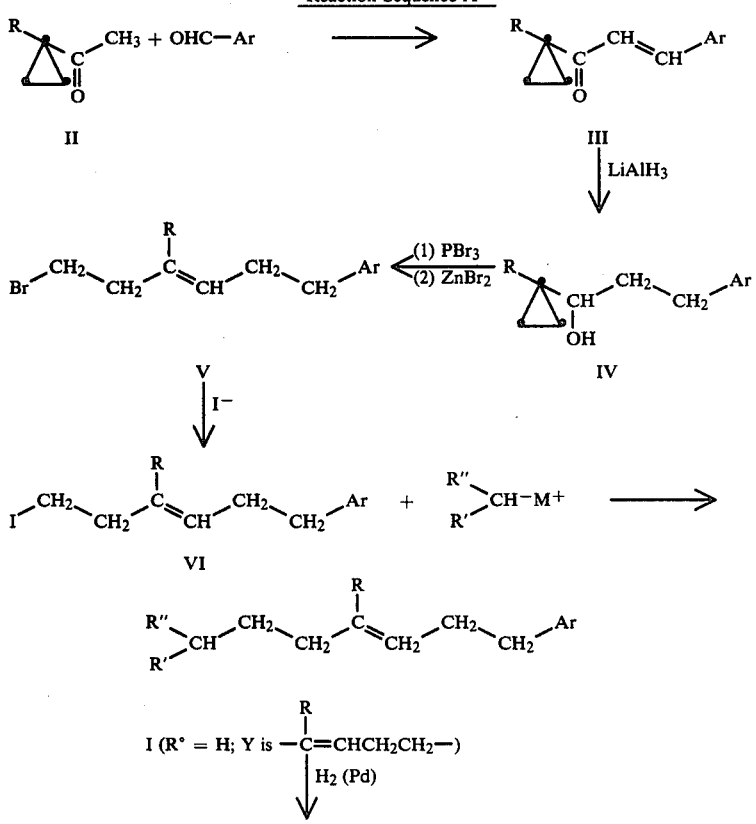

Reaction Sequence A

-continued

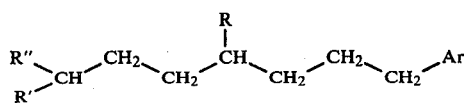

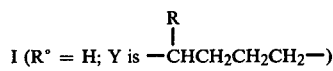

I (R° = H; Y is —CHCH₂CH₂CH₂—)

In the foregoing Reaction Sequence A, a 1-R-1-acetylcyclopropane of formula II, where R has the meaning given hereinabove, is treated with an aldehyde ArCHO in the presence of a base to give the arylvinyl 1-R-cyclopropyl ketone of formula III. The latter, when treated with an alkali metal aluminum hydride, preferably lithium aluminum hydride, is reduced at both the carbonyl group and the olefinic linkage to give an arylethyl 1-R-cyclopropyl carbinol of formula IV. This carbinol is then treated with phosphorus tribromide in the presence of a metal bromide such as lithium bromide to replace the hydroxy group by bromine, which product is then treated with zinc bromide to effect ring opening to form an arylalkenyl bromide of formula V. The latter with a metallic iodide is converted to the corresponding iodide of formula VI. The iodide then is treated with the alkali metal enolate salt of a diketone or keto-ester of formula (R')(R")CH⁻M⁺, where R' and R" have the meanings given hereinabove and M⁺ is an alkali metal, preferably lithium, sodium or potassium. The reaction takes place in an inert solvent under anhydrous conditions and produces a compound of formula I where R° is hydrogen and Y is —C(R)=CHCH₂CH₂—. Catalytic hydrogenation of the latter, for example with palladium, platinum or rhodium catalyst, reduces the olefinic linking to afford a compound of formula I where R° is hydrogen and Y is —CH(R)CH₂CH₂CH₂—.

Alternatively, hydrogenation of the double bond may be performed earlier in the synthesis, upon the unsaturated bromide of formula V. Hydrogenation of the latter in the presence of palladium or platinum oxide catalyst produces a saturated bromide of formula

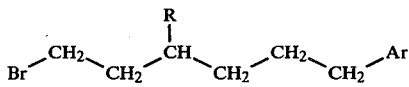

The latter in turn is converted to the corresponding iodide:

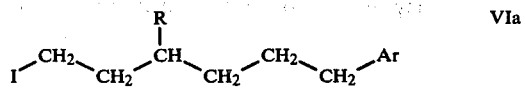

which then is treated with the metallo derivative (R')(R")CH⁻M⁺ to give I (R° is H; Y is —CH(R)CH₂CH₂CH₂).

It has also been found that saturated bromides of formula Va can be caused to react directly with the metallo derivative (R')(R")CH⁻M⁺, without intermediate conversion to the iodides VIa, to form final products of formula I. The iodide reaction takes place at temperatures of 20°-60° C., whereas the bromide reaction requires a higher temperature, about 100°-150° C.

In the event that one or more nitro groups are present in the aromatic nucleus, double bond reductions are carried out by an alternative method in order to avoid reduction of the nitro group(s). This alternative method comprises treating the olefinic compounds with hydroxylamine and hydroxylamine O-sulfonic acid in sodium hydroxide solution [Dürckheimer, Annalen 721, 240 (1969)].

A further alternative approach to compounds within the scope of the present invention involves a Friedel-Crafts type reaction between an aromatic compound, ArH, and an omegahaloalkanoic acid halide. The carbonyl group of the resulting aromatic ketone is subsequently removed by reductive methods to give an arylaliphatic halide which is converted to the compounds of the invention by procedures already described.

Reaction Sequence B

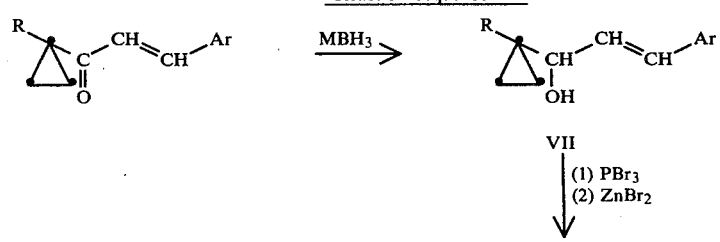

Reaction Sequence B

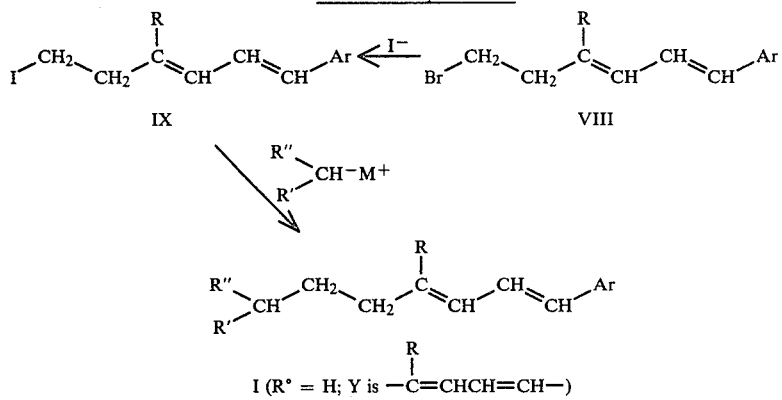

In Reaction Sequence B the arylvinyl 1-R-cyclopropyl ketone of formula III is treated with an alkali metal borohydride, preferably sodium borohydride to reduce the carbonyl group but not the olefinic linkage and provide an arylvinyl 1-R-cyclopropyl carbinol of formula VII. By procedures analogous to those shown in Reaction Sequence A, the carbinol of formula VII is treated with phosphorus tribromide in the presence of a metal bromide and then with zinc bromide to give a diunsaturated aralkyl bromide of formula VIII. The latter is then converted to the corresponding iodide (IX), which reacts with the alkali metal enolate salt of a diketone or keto-ester to afford a compound of formula I where R° is hydrogen and Y is —C(R)=CHCH=CH—. If desired, the latter can be catalytically hydrogenated to produce a compound of formula I where Y is —CH(R)CH$_2$CH$_2$CH$_2$—.

In the event that compounds of formula I where the variable Z defined above is vinylene (—CH=CH—) are desired, the same reaction sequence as in A can be carried out starting with cinnamaldehyde or a substituted cinnamaldehyde of the formula OHC—CH=CH—Ar.

Also, the first step of Reaction Sequence A can be used to produce the corresponding aryl—CH=CH—vinyl 1-R-cyclopropyl ketone for similar use as the starting material in Reaction Sequence B. Catalytic hydrogenation of the compounds where Z is vinylene affords the compounds where Z is ethylene.

If it is desired to obtain compounds of formula I wherein Ar is substituted by from one to three hydroxy groups, the reaction sequences can be carried out with the corresponding compounds where Ar is substituted by from one to three benzyloxy groups. The benzyloxy group or groups can be cleaved by catalytic hydrogenolysis. Any unsaturated linkages in the aliphatic bridge are also hydrogenated at the same time. Alternatively, if it is desired to obtain compounds where Ar is substituted by one or more free hydroxy groups and where the aliphatic bridge is unsaturated, the hydroxy group(s) can be protected throughout the syntheses by esterification (as acetate or benzoate), and the ester hydrolyzed as the final step. The ester protection method is of course also applicable to the preparation of compounds where the aliphatic bridge is saturated.

It is not, however, essential that phenolic hydroxy groups be protected in the form of esters or ethers at the final step of the synthesis because the diketone or keto ester reactant, R'CH$_2$R" is more aidic than the phenolic hydroxyl; hence the desired alkylaion with the iodides or bromides (VI, VIa, Va) will take lace without affecting any phenolic hydroxy groups which ay be present.

The compounds of formula I where the ryl group is substituted by acyloxy can also be prepared y conventional esterification of the corresponding hydrox compounds of formula I with the appropriate acid, acid halide or acid anhydride. The acyloxy groups are derived from carboxylic acids having from one to about ten carbon atoms, and having a molecular weight less than about 200. Representative of the acyl radicals which can be present are lower-alkanoyl radicals, e.g., formyl, acetyl, propionyl, butyryl, isobutyryl, caproyl, heptanoyl, octanoyl, trimethylacetyl, and the like; carboxy-lower-alkanoyl radicals, e.g., succinyl (β-carboxypropionyl); cycloalkyl-lower-alkanoyl radicals, e.g., β-cyclopentylpropionyl, β-cyclohexylpropionyl, and the like; monocarbocyclic aroyl radicals, e.g., benzoyl, p-toluyl, p-nitrobenzoyl, 3,4,5-trimethoxybenzoyl, and the like; monocarboxylic aryl-lower-alkanoyl or -alkenoyl radicals, such as phenylacetyl, β-phenylpropionyl, cinnamoyl, and the like; monocarbocyclic aryloxy-lower-alkanoyl radicals, such as p-chlorophenoxyacetyl and the like; and amino-lower-alkanoyl, such as glycinyl, alaninyl, morpholinobutyryl, and the like. When monocarbocyclic aryl groups are present in the ester moieties, monocarbocyclic aryl includes phenyl and phenyl substituted by from one to three lower-alkyl, lower-alkoxy, halogen or nitro groups.

In the reaction of the arylalkyl iodides or arylalkenyl iodides of formulas VI or IX with the lithium enolate salt of a diketone or keto-ester, some of the iodide reactant undergoes dehydrohalogenation to produce a compound of the formula

The byproducts of formula X are readily separated from the main products of formula I by chromatographic procedures, because the former are of more non-polar character than the latter. Selected compounds of formula X having the structure

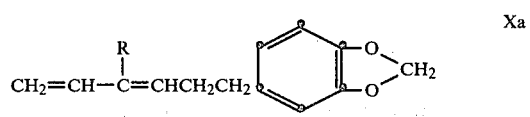

when R is lower-alkyl of 1–4 carbon atoms have been isolated and characterized and are within the purview of the invention. The dehydrohalogenation reaction occurs in the presence of any basic reagent.

The compounds of formula I when R° is chloro can be prepared by treating the corresponding compounds of formula I when R° is hydrogen with a chlorinating agent. An appropriate chlorinating agent is one which introduces a chlorine atom in a position alpha to a carbonyl group. Examples of appropriate chlorinating agents are t-butyl hypochlorite, cupric chloride and sulfuryl chloride.

The compunds of formula I where R° is lower-alkyl can be prepared by treating the corresponding compounds of formula I where R° is hydrogen with a lower-alkyl iodide in the presence of a strong base under anhydrous conditions. The strong base can be an alkali metal alkoxide, hydride or amide, or a strong organic amine such as 1,5-diazabicyclo[5.4.0]undec-5-ene.

The compounds of formula I above where $Z'$ is $CH_2$ or $CH_2CH_2$ are prepared by homologation reactions carried out on the intermediate iodides (formulas VI, VIa, IX). For one-carbon homologation ($Z'$ is $CH_2$), the iodide is interacted with thioanisole and phenyllithium to produce a phenyl thioether where the iodine atom is replaced by $C_6H_5SCH_2$. The phenyl thioether is then heated with methyl iodide which replaces the $C_6H_5S$ group by iodine, yielding the next higher homolog of the original iodide.

For two-carbon homologation ($Z'$ is $CH_2CH_2$), the intermediate iodide of formula VI, VIa or IX is condensed with an alkali metal salt of a malonic ester to give a compound of the formula

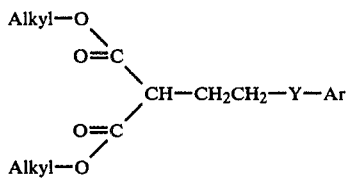    XI

The compound of formula XI is then hydrolyzed and decarboxylated with aqueous alkali to produce a monobasic acid (XII):

    XII

Lithium-aluminum hydride reduction of the latter acid converts it to the alcohol (XIII):

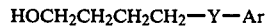    XIII

The latter alcohol is converted to the corresponding iodide by treating its p-toluenesulfonate ester with sodium iodide. The iodide, when condensed with the alkali metal salt of a diketone or keto ester, $(R')(R'')CH^-M^+$, affords compounds of formula I where $Z'$ is $CH_2CH_2$.

A further and preferred aspect of the invention resides in compounds of the formula

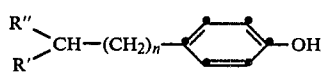    XIV wherein R' and R'' are lower-alkanoyl of 2-6 carbon atoms and n is an integer from 4 to 8, inclusive. The compounds where n is 6-8 can be prepared by methods already described. The compounds where n is 4-5, as well as the compounds where n is 6-8, can be prepared by an alternative synthetic approach starting with anisole. Anisole is subjected to a Friedel-Crafts reaction with an acid halide of the formula $X'(CH_2)_{n-1}COX'$ where $X'$ is chlorine or bromine to give a halo-ketone of the formula $X'(CH_2)_{n-1}COC_6H_4OCH_3(-p)$. The latter is catalytically reduced to a haloalkyl substituted anisole, $X'(CH_2)_nC_6H_4OCH_3(-p)$, which is then converted to the iodide, $I(CH_2)_nC_6H_4OCH_3(-p)$ and demethylated to the phenol, $I(CH_2)_nC_6H_4OH(-p)$. The latter with an alkali metal salt of a diketone $R'CH_2R''$ produces a compound of formula XIV. In the event $X'$ in the compound $X'(CH_2)_nC_6H_4OCH_3(-p)$ is bromine the conversion to the iodide and the demethylation can occur simultaneously by using hydriodic acid.

Biological evaluation of the compounds of formula I and XIV has shown that they possess antiviral activity. They have been found to be effective against one or more of a large variety of RNA and DNA viruses, including Myxoviruses, e.g. influenza types $A_0$, $A_1$, A-2, B; Paramyxoviruses, e.g. parainfluenza types 1, 2, 3, and mumps virus; Picornaviruses, e.g. human rhinoviruses, Coxsackie viruses types A, B, ECHO viruses, equine rhinoviruses; Reoviruses, types 1, 2, 3; Arboviruses, e.g. equine encephalomyelitis (Eastern, Western and Venezuelan), Semliki Forest virus; miscellaneous RNA viruses, e.g. measles, distemper, respiratory syncytial, rubella, vesicular stomatitis, hepatitis; Herpes viruses, e.g. HSV type I, II, herpesvirus simiae, herpesvirus varicellae, infectious bovine rhinotracheitis, cytomegalovirus, Marek's disease virus, Epstein-Barr virus; Poxviruses, e.g. variola, vaccinia; leukemogenic viruses. Both in vitro and in vivo antiviral activity have been found in the compounds of the invention. The in vitro testing of the compounds showed that they had minimal growth inhibitory concentrations (mic) ranging from about 0.3 to about 50 micrograms per milliliter. The mic values were determined by standard serial dilution procedures. Certain of the intermediates of formulas III, IV and VII also showed antiviral activity.

The compounds of formulas I and Xa have also been found to possess pesticidal activity. They showed juvenile hormone-like activity when tested under simulated field conditions in a greenhouse against one or more of the following pest species: yellow mealworm pupae, dock beetle larvae, cabbage looper larvae, yellow fever mosquito larvae and rhodnius prolixus nymph.

The structures of the compounds of the invention were established by the modes of synthesis, by elementary analysis, and by infrared and nuclear magnetic resonance spectral determinations.

A further aspect of the invention relates to compositions for combatting arthropods by hindering the maturation thereof which comprise an effective amount of at least one compound of formula I in admixture with a suitable carrier or diluent, and to the method of combatting arthropods at any stage of their development by contacting them with said compositions.

The compositions of the invention are effective against insects at any stage of their development short of the final adult form, i.e. at the egg, larval or pupal stages. The compounds can be formulated in conventional manner as solutions, emulsions, suspensions, dusts and aerosol sprays. The pesticide compositions of the invention can contain adjuvants found normally in such preparations, including water and/or organic solvents such as acetone, dimethylformamide, sesame oil, petroleum oils, and the like. Emulsifying and surface active agents may also be added. Dust formulations can contain talc, diatomaceous earth, kaolin, bentonite, calcium carbonate, wood, flour, cork, carbon, and the like. The aerosol sprays contain propellants such as dichlorodifluoromethane. The compounds of this invention can be employed as the sole pesticide component or they can be used in admixture with other compounds having similar utility. While the concentration of active ingredient can vary within rather wide limits, ordinarily the pesticide will comprise not more than about 10%, and preferably about 1% by weight of the composition.

A still further object of the invention relates to compositions for combatting viruses which comprise an antivirally effective amount of at least one compound of formula I in admixture with a suitable carrier or diluent, and to the method of combatting viruses by contacting the locus of said viruses with said compositions.

The antiviral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams.

The following examples will further illustrate the invention.

PREPARATION OF INTERMEDIATES

A. 2-Arylvinyl cyclopropyl ketones (III)

A1. 2-(3,4-Methylenedioxyphenyl)vinyl 1-ethylcyclopropyl ketone [III; Ar is 3,4-methylenedioxyphenyl, R is $C_2H_5$].

A mixture of 33.6 g. (0.3 mole) of 1-ethylcyclopropyl methyl ketone and 45 g. (0.3 mole) of piperonal in 21 ml. of ethanol was stirred at room temperature, and 21 ml. of 20% aqueous sodium hydroxide was added dropwise over a period of 30-45 minutes. The mixture was warmed at 40°-60° C. for three hours with stirring. The solution was then cooled to 0°-10° C., 0.2 ml. of glacial acetic acid added, and the mixture was extracted with ether. The ether extracts were concentrated, and the residue dissolved in 200 ml. of 95% ethanol, which solution when cooled caused separation of a solid product. The latter was recrystallized from 150 ml. of methanol to give 39 g. of 2-(3,4-methylenedioxyphenyl)vinyl 1-ethylcyclopropyl ketone, m.p. 62°-64° C.

A2. 2-(3,4-Methylenedioxyphenyl)vinyl cyclopropyl ketone [III; Ar is 3,4-methylenedioxyphenyl, R is H] was prepared from 8.4 g. of cyclopropyl methyl ketone and 15 g. of piperonal according to the procedure described above in Preparation A1 affording 21.5 g., m.p. 85°-87° C. when recrystallized from ethanol.

A3. 2-(3,4-Methylenedioxyphenyl)vinyl 1-methylcyclopropyl ketone [III; Ar is 3,4-methylenedioxyphenyl, R is $CH_3$] was prepared from 25.6 g. of 1-methylcyclopropyl methyl ketone and 9.3 g. of piperonal according to the procedure described above in Preparation A1, affording 29.5 g. of crystalline product.

A4. 2-(3,4-Dimethoxyphenyl)vinyl 1-ethylcyclopropyl ketone [III; Ar is 3,4-$(CH_3O)_2C_6H_3$, R is $C_2H_5$] was prepared from 22.4 g. of 1-ethylcyclopropyl methyl ketone and 33.2 g. of veratraldehyde according to the procedure described above in Preparation A1, affording 20.3 g., b.p. 156°-158° C. (0.02 mm.).

A5. 2-(4-Methoxyphenyl)vinyl cyclopropyl ketone [III; Ar is 4-$CH_3OC_6H_4$, R is ] was prepared from 84.1 g. of cyclopropyl methyl ketone and 136 g. of p-methoxybenzaldehyde according to the procedure described above in Preparation A1, affording 173.5 g., m.p. 70°-72° C. when recrystallized from ethanol.

A6. 2-Phenylvinyl cyclopropyl ketone [III; Ar is $C_6H_5$, R is H] was prepared from 13.5 g. of cyclopropyl methyl ketone and 17.1 g. of benzaldehyde according to the procedure described above in Preparation A1, affording 23.0 g., m.p. 58°-60° C. when recrystallized from absolute ethanol.

A7. 2-(4-Chlorophenyl)vinyl cyclopropyl ketone [III; Ar is 4-$ClC_6H_4$, R is H] was prepared from 25.2 g. of cyclopropyl methyl ketone and 42 g. of p-chlorobenzaldehyde according to the procedure described above in Preparation A1, affording 31 g., m.p. 63°-65° C. when recrystallized from ethanol.

A8. 2-(p-Tolyl)vinyl cyclopropyl ketone [III; Ar is 4-$CH_3C_6H_4$, R is H] was prepared from 84.1 g. of cyclopropyl methyl ketone in 120 g. of p-tolualdehyde according to the procedure described above in Preparation A1, affording 158.7 g., colorless plates, m.p. 78°-80° C. when recrystallized from ethanol.

A9. 2-(4-Carboxyphenyl)vinyl 1-ethylcyclopropyl ketone [III; Ar is 4-$HO_2CC_6H_4$, R is $C_2H_5$] was prepared from 67.2 g. of 1-ethylcyclopropyl methyl ketone and 90 g. of p-carboxybenzaldehyde according to the procedure described above in Preparation A1, affording 40 g., m.p. 183.5°-184.5° C. when recrystallized from acetonitrile and then repeatedly from isopropyl alcohol.

By following the procedure of Preparation A1 above, 1-isopropylcyclopropyl methyl ketone or 1-butylcyclopropyl methyl ketone can be caused to react with piperonal to give 2-(3,4-methylenedioxyphenyl)vinyl 1-isopropylcyclopropyl ketone [III; Ar is 3,4-methylenedioxyphenyl, R is $(CH_3)_2CH$], or 2-(3,4-methylenedioxyphenyl)vinyl 1-butylcyclopropyl ketone [III; Ar is 3,4-methylenedioxyphenyl, R is $CH_3CH_2CH_2$], respectively.

By following the procedure of Preparation A1 above, cyclopropyl methyl ketone can be caused to react with 3,4-dichlorobenzaldehyde, 2,4-dichlorobenzaldehyde, 4-bromobenzaldehyde, 4-fluorobenzaldehyde, 4-hydroxybenzaldehyde, 4-trifluoromethoxybenzaldehyde or 4-trifluoromethylbenzaldehyde to give, respectively, 2-(3,4-dichlorophenyl)vinyl cyclopropyl ketone [III; Ar is 3,4-$Cl_2C_6H_3$, R is H], 2-(2,4-dichlorophenyl)vinyl cyclopropyl ketone [III; Ar is 2,4-$Cl_2C_6H_3$, R is H], 2-(4-bromophenyl)vinyl cyclopropyl ketone [III; Ar is 4-$BrC_6H_4$, R is H], 2-(4-fluorophenyl)vinyl cyclopropyl ketone [III; Ar is 4-$FC_6H_4$, R is H], 2-(4-hydroxyphenyl)vinyl cyclopropyl ketone [III; Ar is 4-$HOC_6H_4$, R is H], 2-(4-trifluoromethoxyphenyl)vinyl cyclopropyl ketone [III; Ar is 4-$F_3COC_6H_4$, R is H], or 2-(4-trifluoromethylphenyl)vinyl cyclopropyl ketone [III; Ar is 4-$F_3CC_6H_4$, R is H]. 2-(4-Hydroxyphenyl)vinyl cyclopropyl ketone can be esterified with benzoyl chloride to give 2-(4-benzoyloxyphenyl)vinyl cyclopropyl ketone [III; Ar is 4-$C_6H_5COOC_6H_4$, R is H].

According to the procedures of Preparations A1-A9 using the appropriate starting materials, the following compounds were prepared:

A10. 2-(2,4-Dichlorophenyl)vinyl cyclopropyl ketone [III; Ar is 2,4-Cl$_2$C$_6$H$_3$, R is H], yellow solid, m.p. 85°-87° C. (from isopropyl alcohol).

A11. 2-(4-Acetamidophenyl)vinyl cyclopropyl ketone [III; Ar is 4-CH$_3$CONHC$_6$H$_4$, R is H], yellow crystals, m.p. 191°-192° C.

A12. 1-Cyclopropyl-5-(p-methoxyphenyl)-2,4-pentadien-1-one, C$_3$H$_5$COCH=CHCH=CH—C$_6$H$_4$OCH$_3$—4, yellow solid, m.p. 131°-132.5° C. (from ethanol) prepared from 4-methoxycinnamaldehyde and cyclopropyl methyl ketone.

A13. 2-(4-Dimethylaminophenyl)vinyl cyclopropyl ketone [III; Ar is 4-(CH$_3$)$_2$NC$_6$H$_4$, R is H], yellow solid, m.p. 137°-139° C. (from ethanol), active against equine rhino virus in vitro at 12 micrograms per milliliter.

A14. 2-(4-Benzyloxyphenyl)vinyl cyclopropyl ketone [III; Ar is 4-C$_6$H$_5$CH$_2$OC$_6$H$_4$, R is H], cream-colored solid, m.p. 111°-113° C. (from ethanol), active against equine rhino virus in vitro at 12 micrograms per milliliter.

A15. 2-(3,4-Dibenzyloxyphenyl)vinyl cyclopropyl ketone [III; Ar is 3,4-(C$_6$H$_5$CH$_2$O)$_2$C$_6$H$_3$, R is H], cream-colored solid, m.p. 100°-102° C. (from methanol), active against equine rhino virus in vitro at 1.5 micrograms per milliliter.

A16. 2-(4-Trifluoromethoxyphenyl)vinyl cyclopropyl ketone [III; Ar is 4-F$_3$COC$_6$H$_4$, R is H].

A17. 2-(1-Naphthyl)vinyl cyclopropyl ketone [III; Ar is 1-naphthyl, R is H].

A18. 2-(4-Fluorophenyl)vinyl cyclopropyl ketone [III; Ar is 4-FC$_6$H$_4$, R is H].

A19. 2-(4-Diethylaminophenyl)vinyl cyclopropyl ketone [III; Ar is 4-(C$_2$H$_5$)$_2$NC$_6$H$_4$, R is H], yellow solid, m.p. 79°-81° C. (from ethanol).

A20. 2-(4-Benzyloxy-3,5-dimethoxyphenyl)vinyl cyclopropyl ketone [III; Ar is 3,5-(CH$_3$O)$_2$-4-C$_6$H$_5$CH$_2$OC$_6$H$_2$, R is H], light yellow crystals, m.p. 98°-99° C. (from ethanol).

A21. 2-(3-Iodo-4-methoxyphenyl)vinyl cyclopropyl ketone [III; Ar is 3-I-4-CH$_3$OC$_6$H$_3$, R is H], light yellow solid, m.p. 89°-90° C., active against equine rhino virus in vitro at 6 micrograms per milliliter.

B. 2-Arylethyl cyclopropyl carbinols (IV) and 2-arylvinyl cyclopropyl carbinols (VII)

B1. 2-(3,4-Methylenedioxyphenyl)ethyl 1-ethylcyclopropyl carbinol [IV; Ar is 3,4-methylenedioxyphenyl, R is C$_2$H$_5$].

A suspension of 15 g. of lithium aluminum hydride in about 500 ml. of tetrahydrofuran was heated at reflux while a solution of 60 g. of 2-(3,4-methylenedioxyphenyl)vinyl 1-ethylcyclopropyl ketone (Preparation A1) in 150 ml. of tetrahydrofuran was added dropwise over a period of 2-3 hours. The reaction mixture was heated at reflux for two hours, cooled, and then water was added very cautiously. Excess anhydrous sodium sulfate was added, the mixture filtered, and the filter cake washed several times with chloroform. The combined filtrate and washings were evaporated to dryness to give 53 g. of an oil consisting of 2-(3,4-methylenedioxyphenyl)ethyl 1-ethylcyclopropyl carbinol.

B2. 2-(3,4-Methylenedioxyphenyl)ethyl cyclopropyl carbinol [IV; Ar is 3,4-methylenedioxyphenyl, R is H] was prepared from 18.4 g. of 2-(3,4-methylenedioxyphenyl)vinyl cyclopropyl ketone (Preparation A2) and 3.1 g. of lithium aluminum hydride according to the procedure described above in Preparation B1, affording 11.5 g., b.p. 116°-122° C. (0.005 mm.), m.p. 64°-65° C. when recrystallized from ether.

B3. 2-(3,4-Methylenedioxyphenyl)ethyl 1-methylcyclopropyl carbinol [IV; Ar is 3,4-methylenedioxyphenyl, R is CH$_3$] was prepared from 23.4 g. of 2-(3,4-methylenedioxyphenyl)vinyl 1-methylcyclopropyl ketone (Preparation A3) and 3.88 g. of lithium aluminum hydride according to the procedure described above in Preparation B1, affording 18.8 g., b.p. 120°-130° C. (0.003 mm.).

B4. 2-(3,4-Dimethoxyphenyl)ethyl 1-ethylcyclopropyl carbinol [IV; Ar is 3,4-(CH$_3$O)$_2$C$_6$H$_3$, R is C$_2$H$_5$] was prepared from 15 g. of 2-(3,4-dimethoxyphenyl)vinyl 1-ethylcyclopropyl ketone (Preparation A4) and 2.2 g. of lithium aluminum hydride according to the procedure described above in Preparation B1, affording 10 g., b.p. 148°-150° C. (0.01 mm.).

B5. 2-(4-Methoxyphenyl)ethyl cyclopropyl carbinol [IV; Ar is 4-CH$_3$OC$_6$H$_4$, R is H] was prepared from 50 g. of 2-(4-methoxyphenyl)vinyl cyclopropyl ketone (Preparation A5) and 9.7 g. of lithium aluminum hydride according to the procedure described above in Preparation B1, affording 42 g., b.p. 116°-117° C. (0.05 mm.).

B6. 2-Phenylethyl cyclopropyl carbinol [IV; Ar is C$_6$H$_5$, R is H] was prepared from 23 g. of 2-phenylvinyl cyclopropyl ketone (Preparation A6) and 5.22 g. of lithium aluminum hydride according to the procedure described above in Preparation B1, affording 18.5 g., b.p. 89°-90° C. (0.02 mm.).

B7. 2-(4-Chlorophenyl)ethyl cyclopropyl carbinol [IV; Ar is 4-ClC$_6$H$_4$, R is H] was prepared from 31 g. of 2-(4-chlorophenyl)vinyl cyclopropyl ketone (Preparation A7) and 5.87 g. of lithium aluminum hydride according to the procedure described above in Preparation B1, affording 23.8 g., b.p. 105°-106° C. (0.1 mm.).

B8. 2-(p-Tolyl)ethyl cyclopropyl carbinol [IV; Ar is 4-CH$_3$C$_6$H$_4$, R is H] was prepared from 158 g. of 2-(p-tolyl)vinyl cyclopropyl ketone (Preparation A8) and 33.2 g. of lithium aluminum hydride according to the procedure described above in Preparation B1, affording 137 g., b.p. 97°-98° C. (0.13 mm.).

B9. 2-(4-Carboxyphenyl)vinyl 1-ethylcyclopropyl carbinol [VII; Ar is 4-HO$_2$CC$_6$H$_4$, R is C$_2$H$_5$].

To a stirred suspension of 34.0 g. of 2-(4-carboxyphenyl)vinyl 1-ethylcyclopropyl ketone (Preparation A9) in 500 ml. of ice water was slowly added 11 g. of sodium borohydride over a one hour period. The mixture was stirred for about sixteen hours and then cautiously acidified with ice-cold concentrated hydrochloric acid. The solid material was collected by filtration and dissolved in ether. The ether solution was dried over anhydrous magnesium sulfate and concentrated to give 33.2 g. of 2-(4-carboxyphenyl)vinyl 1-ethylcyclopropyl carbinol, m.p. 130°-131° C. when recrystallized from toluene.

B10. 2-(4-Carboxyphenyl)ethyl 1-ethylcyclopropyl carbinol [IV; Ar is 4-HO$_2$CC$_6$H$_4$, R is C$_2$H$_5$].

A solution of 29 g. of 2-(4-carboxyphenyl)vinyl 1-ethylcyclopropyl carbinol (Preparation B9) in 200 ml. of ethanol was hydrogenated in the presence of 1 g. of palladium-on-carbon catalyst. There was thus obtained 28 g. of 2-(4-carboxyphenyl)ethyl 1-ethylcyclopropyl carbinol, colorless crystals, m.p. 116°-117.5° C.

B11. 2-(3,4-Methylenedioxyphenyl)vinyl 1-ethylcyclopropyl carbinol [VII; Ar is 3,4-methylenedioxyphenyl, R is C$_2$H$_5$].

To a cold solution of 5 g. of 2-(3,4-methylenedioxyphenyl)vinyl 1-ethylcyclopropyl ketone (Preparation A1) in 50 ml. of methanol was added in portions 1.56 g. of sodium borohydride. The mixture was stirred at room temperature for two hours, then diluted with water and extracted with ether. The ether extracts were dried and concentrated to give 3.6 g. of 2-(3,4-methylenedioxyphenyl)vinyl 1-ethylcyclopropyl carbinol as a colorless oil.

By replacing the 2-(3,4-methylenedioxyphenyl)vinyl 1-ethylcyclopropyl ketone in Preparation B1 above by a molar equivalent amount of 2-(3,4-methylenedioxyphenyl)vinyl 1-isopropylcyclopropyl ketone, 2-(3,4-methylenedioxyphenyl)vinyl 1-butylcyclopropyl ketone, 2-(3,4-dichlorophenyl)vinyl cyclopropyl ketone, 2-(2,4-dichlorophenyl)vinyl cyclopropyl ketone, 2-(4-bromophenyl)vinyl cyclopropyl ketone, 2-(4-fluorophenyl)vinyl cyclopropyl ketone, 2-(4-benzoyloxyphenyl)vinyl cyclopropyl ketone, 2-(4-trifluoromethoxyphenyl)vinyl cyclopropyl ketone or 2-(4-trifluoromethylphenyl)vinyl cyclopropyl ketone there can be obtained, respectively, 2-(3,4-methylenedioxyphenyl)ethyl 1-isopropylcyclopropyl carbinol [IV; Ar is 3,4-methylenedioxyphenyl, R is $(CH_3)_2CH$], 2-(3,4-methylenedioxyphenyl)ethyl 1-butylcyclopropyl carbinol [IV; Ar is 3,4-methylenedioxyphenyl, R is $CH_3CH_2CH_2CH_2$], 2-(3,4-dichlorophenyl)ethyl cyclopropyl carbinol [IV; Ar is $3,4$-$Cl_2C_6H_3$, R is H], 2-(2,4-dichlorophenyl)ethyl cyclopropyl carbinol [IV; Ar is $2,4$-$Cl_2C_6H_3$, R is H], 2-(4-bromophenyl)ethyl cyclopropyl carbinol [IV; Ar is $4$-$BrC_6H_4$, R is H], 2-(4-fluorophenyl)ethyl cyclopropyl carbinol [IV; Ar is $4$-$FC_6H_4$, R is H], 2-(4-benzoyloxyphenyl)ethyl cyclopropyl carbinol [IV; Ar is $4$-$C_6H_5COOC_6H_4$, R is H], 2-(4-trifluoromethoxyphenyl)ethyl cyclopropyl carbinol [IV; Ar is $4$-$F_3COC_6H_4$, R is H], or 2-(4-trifluoromethylphenyl)ethyl cyclopropyl carbinol [IV; Ar is $4$-$F_3CC_6H_4$, R is H].

According to the procedure of Preparations B1–B11 using the appropriate starting materials, the following compounds were prepared:

B12. 2-(2,4-Dichlorophenyl)ethyl cyclopropyl carbinol [IV; Ar is $2,4$-$Cl_2C_6H_3$, R is H], b.p. 119°–126° C. (0.2 mm.), prepared from compound of Preparation A10.

B13. 2-(4-Acetamidophenyl)ethyl cyclopropyl carbinol [IV; Ar is $4$-$CH_3CONHC_6H_4$, R is H], m.p. 142°–143° C., prepared from compound of Preparation A11.

B14. 4-(4-Methoxyphenyl)-3-butenyl cyclopropyl carbinol, $C_3H_5CH(OH)CH_2CH_2CH=CHC_6H_4OCH_3$-4, b.p. 131°–132° C. (0.1 mm.), prepared from compound of Preparation A12.

B15. 2-(4-Dimethylaminophenyl)vinyl cyclopropyl carbinol [VII; Ar is $4$-$(CH_3)_2NC_6H_4$, R is H], cream-colored solid, m.p. 76°–78° C. (from ethanol-pentane), prepared from compound of Preparation A13.

B16. 2-(4-Dimethylaminophenyl)ethyl cyclopropyl carbinol [IV; Ar is $4$-$(CH_3)_2NC_6H_4$, R is H], pale yellow oil, b.p. 126°–128° C. (0.2 mm.), prepared from compound of Preparation A13, active against equine rhino virus in vitro at 12 micrograms per milliliter.

B17. 2-(4-Benzyloxyphenyl)ethyl cyclopropyl carbinol [IV; Ar is $4$-$C_6H_5CH_2OC_6H_4$, R is H], m.p. 76°–77° C. (from ether-pentane), prepared from compound of Preparation A14.

B18. 2-(3,4-Dibenzyloxyphenyl)ethyl cyclopropyl carbinol [IV; Ar is $3,4$-$(C_6H_5CH_2O)_2C_6H_3$, R is H], m.p. 62°–64° C. (from etherpentane), prepared from compound of Preparation A15, active against equine rhino virus in vitro at 6 micrograms per milliliter.

B19. 2-(4-Trifluoromethoxyphenyl)ethyl cyclopropyl carbinol [IV; Ar is $4$-$F_3COC_6H_4$, R is H], prepared from compound of Preparation A16.

B20. 2-(1-Naphthyl)ethyl cyclopropyl carbinol [IV; Ar is 1-naphthyl, R is H], b.p. 145°–146° C. (0.01 mm.), prepared from compound of Preparation A17.

B21. 2-(4-Fluorophenyl)ethyl cyclopropyl carbinol [IV; Ar is $4$-$FC_6H_4$, R is H], b.p. 90°–93° C. (0.2 mm.), prepared from compound of Preparation A18.

B22. 2-(4-Diethylaminophenyl)ethyl cyclopropyl carbinol [IV; Ar is $4$-$(C_2H_5)_2NC_6H_4$, R is H], pale yellow oil, b.p. 129°–131° C. (0.15 mm.), prepared from compound of Preparation A19.

B23. 2-(4-Benzyloxy-3,5-dimethoxyphenyl)ethyl cyclopropyl carbinol [IV; Ar is $3,5$-$(CH_3O)_2$-$4$-$C_6H_5CH_2OC_6H_2$, R is H], prepared from compound of Preparation A20.

C. Arylalkenyl bromides (V, VIII) and arylalkyl bromides (Va)

C1. 3-Ethyl-6-(3,4-methylenedioxyphenyl)-3-hexenyl bromide [V; Ar is 3,4-methylenedioxyphenyl, R is $C_2H_5$].

To a solution of 26.4 g. (0.106 mole) of 2-(3,4-methylenedioxyphenyl)ethyl 1-ethylcyclopropyl carbinol in 250 ml. of ether, cooled to −30° C. under nitrogen, was added 18 ml. of collidine. Lithium bromide (26 g., 0.3 mole) was then added, the mixture cooled to −50° C. and 25 g. (0.09 mole) of phosphorus tribromide was added dropwise. The reaction mixture was stirred at −50° C. for ten minutes, allowed to warm to 0° C. over a three hour period and stirred at 0° C. for three hours. Collidine (30 ml.) was added, followed by 10 ml. of water. The reaction mixture was partitioned between water and ether, the ether layer washed with water and sodium chloride solution, and dried over anhydrous magnesium sulfate. The ether solution was concentrated to give an oily product used directly in the following reaction.

The latter product was dissolved in about 200 ml. of anhydrous ether and added in a fine stream to a stirred mixture of 27 g. of zinc bromide in 200 ml. of ether held at −30° to −35° C. The mixture was stirred, then allowed to warm to 0° C. during two hours, held there for thirty minutes, and then allowed to warm to room temperature over a three hour period and stirred for two hours longer. The reaction mixture was partitioned between ether and aqueous sodium chloride. The ether layer was washed three times with 500 ml. of water, then with sodium chloride solution, dried over anhydrous magnesium sulfate and concentrated to remove the solvent. The residue was redissolved in ether, washed with dilute aqueous sodium bicarbonate and with sodium chloride solution, and evaporated to give 23 g. of 3-ethyl-6-(3,4-methylenedioxyphenyl)-3-hexenyl bromide as a straw-colored oil.

C2. 6-(3,4-Methylenedioxyphenyl)-3-hexenyl bromide [V; Ar is 3,4-methylenedioxyphenyl, R is H] was prepared from 11.5 g. of 2-(3,4-methylenedioxyphenyl)ethyl cyclopropyl carbinol (Preparation B2), 12 g. of phosphorus tribromide, 10 g. of lithium bromide and 12.7 g. of zinc bromide according to the procedure given above in Preparation C1, affording 12.5 g. of product as an oil.

C3. 3-Methyl-6-(3,4-methylenedioxyphenyl)-3-hexenyl bromide [V; Ar is 3,4-methylenedioxyphenyl, R is CH$_3$] was prepared from 17.6 g. of 2-(3,4-methylenedioxyphenyl)ethyl 1-methylcyclopropyl carbinol (Preparation B3), 20.3 g. of phosphorus tribromide, 18.5 g. of lithium bromide and 21 g. of zinc bromide according to the procedure given above in Preparation C1, affording 19 g. of product as an oil.

C4. 3-Ethyl-6-(3,4-dimethoxyphenyl)-3-hexenyl bromide [V; Ar is 3,4-(CH$_3$O)$_2$C$_6$H$_3$, R is C$_2$H$_5$] was prepared from 16 g. of 2-(3,4-dimethoxyphenyl)ethyl 1-ethylcyclopropyl carbinol (Preparation B4), 16.8 g. of phosphorus tribromide, 16.8 g. of lithium bromide and 17.6 g. of zinc bromide according to the procedure given above in Preparation C1. The product was used directly in the succeeding step (Preparation D4) without isolation.

C5. 6-(4-Methoxyphenyl)-3-hexenyl bromide [V; Ar is 4-CH$_3$OC$_6$H$_4$, R is H] was prepared from 38.2 g. of 2-(4-methoxyphenyl)ethyl cyclopropyl carbinol (Preparation B5), 42.5 g. of phosphorus tribromide, 35 g. of lithium bromide and 40 g. of zinc bromide according to the procedure given above in Preparation C1, affording 48 g. of product as an oil.

C6. 6-Phenyl-3-hexenyl bromide [V; Ar is C$_6$H$_5$, R is H] was prepared from 16.5 g. of 2-phenylethyl cyclopropyl carbinol (Preparation B6), 21.5 g. of phosphorus tribromide, 17.65 g. of lithium bromide and 20.7 g. of zinc bromide according to the procedure given above in Preparation C1, affording 21 g. of product as a pale yellow oil.

C7. 6-(4-Chlorophenyl)-3-hexenyl bromide [V; Ar is 4-ClC$_6$H$_4$, R is H] was prepared from 21 g. of 2-(4-chlorophenyl)ethyl cyclopropyl carbinol (Preparation B7), 23 g. of phosphorus tribromide, 18.85 g. of lithium bromide and 22.5 g. of zinc bromide according to the procedure given above in Preparation C1, affording 25.5 g. of product as an oil.

C8. 6-(p-Tolyl)-3-hexenyl bromide [V; Ar is 4-CH$_3$C$_6$H$_4$, R is H] was prepared from 2-(p-tolyl)ethyl cyclopropyl carbinol (Preparation B8), phosphorus tribromide, lithium bromide and zinc bromide according to the procedure given above in Preparation C1.

C9. 3-Ethyl-6-(4-carbomethoxyphenyl)-3-hexenyl bromide [V; Ar is 4-CH$_3$O$_2$CC$_6$H$_4$, R is C$_2$H$_5$].

A mixture of 21.3 g. of 2-(4-carboxyphenyl)vinyl 1-ethylcyclopropyl carbinol (Preparation B9) and 500 ml. of methanol saturated with hydrogen chloride at 0° C. was stirred for one hour at 0° C. and then allowed to come to room temperature with stirring until the solution was complete. The reaction mixture was concentrated to dryness, the residue taken up in chloroform and washed with water and sodium bicarbonate solution, dried over anhydrous magnesium sulfate and concentrated to give 24.4 g. of a light yellow oil. The latter product was dissolved in a small quantity of ether and added to a solution of 700 g of zinc bromide in 4 liters of anhydrous ether. The reaction mixture was stirred for twenty hours, then washed with water, dried over anhydrous magnesium sulfate and the solvent evaporated, affording 17.5 g. of 3-ethyl-6-(4-carbomethoxyphenyl)-3-hexenyl bromide as a light yellow oil.

C10. 3-Ethyl-6-(3,4-methylenedioxyphenyl)-3,5-hexadienyl bromide [VIII; Ar is 3,4-methylenedioxyphenyl, R is C$_2$H$_5$] was prepared from 3.6 g. of 2-(3,4-methylenedioxyphenyl)vinyl 1-ethylcyclopropyl carbinol (Preparation B11), 3.5 g. of phosphorus tribromide, 4.5 g. of lithium bromide and 3.5 g. of zinc bromide according to the procedure given above in Preparation C1, affording 2 g. of product as an oil.

C11. 6-(4-Methoxyphenyl)hexyl bromide [Va; Ar is 4-CH$_3$OC$_6$H$_4$, R is H].

A mixture of 18.6 g. of 6-(4-methoxyphenyl)-3-hexenyl bromide (Preparation C5) and 0.21 g. of platinum oxide catalyst in 200 ml. of isopropyl alcohol was hydrogenated until 1 mole equivalent of hydrogen had been absorbed. The product was isolated and distilled to give 12.8 g. of 6-(4-methoxyphenyl) hexyl bromide, b.p. 126°–128° C. (0.04 mm.).

C12. 6-Phenylhexyl bromide [Va; Ar is C$_6$H$_5$, R is H] was prepared by hydrogenation of 21 g. of 6-phenyl-3-hexenyl bromide (Preparation C6) according to the procedure described above in Preparation C11, affording 16 g., b.p. 86°–87° C. (0.02 mm.).

C13. 6-(4-Chlorophenyl)hexyl bromide [Va; Ar is 4-ClC$_6$H$_4$, R is H] was prepared by hydrogenation of 25.2 g. of 6-(4-chlorophenyl)-3-hexenyl bromide (Preparation C7) according to the procedure described above in Preparation C11, affording 17 g., b.p. 110°–111° C. (0.02 mm.).

C14. 6-(p-Tolyl)hexyl bromide [Va; Ar is 4-CH$_3$C$_6$H$_4$, R is H] was prepared by hydrogenation of 6-(p-tolyl)-3-hexenyl bromide according to the procedure described above in Preparation C11.

By replacing the 2-(3,4-methylenedioxyphenyl)ethyl 1-ethylcyclopropyl carbinol in Preparation C1 by a molar equivalent amount of 2-(3,4-methylenedioxyphenyl)ethyl 1-isopropylcyclopropyl carbinol, 2-(3,4-methylenedioxyphenyl)ethyl 1-butylcyclopropyl carbinol, 2-(3,4-dichlorophenyl)ethyl cyclopropyl carbinol, 2-(2,4-dichlorophenyl)ethyl cyclopropyl carbinol, 2-(4-bromophenyl)ethyl cyclopropyl carbinol, 2-(4-fluorophenyl)ethyl cyclopropyl carbinol, 2-(4-benzoyloxyphenyl)ethyl cyclopropyl carbinol, 2-(4-trifluoromethoxyphenyl)ethyl cyclopropyl carbinol or 2-(4-trifluoromethylphenyl)ethyl cyclopropyl carbinol there can be obtained, respectively, 3-isopropyl-6-(3,4-methylenedioxyphenyl)-3-hexenyl bromide [V; Ar is 3,4-methylenedioxyphenyl, R is (CH$_3$)$_2$CH], 3-butyl-6-(3,4-methylenedioxyphenyl)-3-hexenyl bromide [V; Ar is 3,4-methylenedioxyphenyl, R is CH$_3$CH$_2$CH$_2$CH$_2$], 6-(3,4-dichlorophenyl)-3-hexenyl bromide [V; Ar is 3,4-Cl$_2$C$_6$H$_3$, R is H], 6-(2,4-dichlorophenyl)-3-hexenyl bromide [V; Ar is 2,4-Cl$_2$C$_6$H$_3$, R is H], 6-(4-bromophenyl)-3-hexenyl bromide [V; Ar is 4-BrC$_6$H$_4$, R is H], 6-(4-fluorophenyl)-3-hexenyl bromide [V; Ar is 4-FC$_6$H$_4$, R is H], 6-(4-benzoyloxyphenyl)-3-hexenyl bromide [V; Ar is 4-C$_6$H$_5$COOC$_6$H$_4$, R is H], 6-(4-trifluoromethoxyphenyl)-3-hexenyl bromide [V; Ar is 4-F$_3$COC$_6$H$_4$, R is H], or 6-(4-trifluoromethylphenyl)-3-hexenyl bromide [V; Ar is 4-F$_3$CC$_6$H$_4$, R is H].

The latter products can be hydrogenated according to the procedure of Preparation C11 to give, respectively, 3-isopropyl-6-(3,4-methylenedioxyphenyl)hexyl bromide [Va; Ar is 3,4-methylenedioxyphenyl, R is (CH$_3$)$_2$CH], 3-butyl-6-(3,4-methylenedioxyphenyl)hexyl bromide [Va; Ar is 3,4-methylenedioxyphenyl, R is CH$_3$CH$_2$CH$_2$CH$_2$], 6-(3,4-dichlorophenyl)hexyl bromide [Va; Ar is 3,4-Cl$_2$C$_6$H$_3$, R is H], 6-(2,4-dichlorophenyl)hexyl bromide [Va; Ar is 2,4-Cl$_2$C$_6$H$_3$, R is H], 6-(4-bromophenyl)hexyl bromide [Va; Ar is 4-BrC$_6$H$_4$, R is H], 6-(4-fluorophenyl)hexyl bromide [Va; Ar is 4-FC$_6$H$_4$, R is H], 6-(4-trifluoromethoxyphenyl)hexyl bromide [Va; Ar is 4-F$_3$COC$_6$H$_4$, R is H], or 6-(4-trifluoromethylphenyl)hexyl bromide [Va; Ar is 4-F$_3$CC$_6$H$_4$, R is H].

According to the procedures of Preparations C1–C14 using the appropriate starting materials, the following compounds were prepared:

C15. 6-(2,4-Dichlorophenyl)-3-hexenyl bromide [V; Ar is 2,4-Cl$_2$C$_6$H$_3$, R is H], prepared from compound of Preparation B12.

C16. 6-(2,4-Dichlorophenyl)hexyl bromide [Va; Ar is 2,4-Cl$_2$C$_6$H$_3$, R is H], prepared by hydrogenation of the compound of Preparation C15.

C17. 6-(4-Acetamidophenyl)-3-hexenyl bromide [V; Ar is 4-CH$_3$CONHC$_6$H$_4$, R is H], prepared from the compound of Preparation B13.

C18. 8-(4-Methoxyphenyl)-3,7-octadienyl bromide, BrCH$_2$CH$_2$CH=CHCH$_2$CH$_2$CH=CHC$_6$H$_4$OCH$_3$-4, prepared from the compound of Preparation B14.

C19. 6-(4-Dimethylaminophenyl)-3-hexenyl bromide [V; Ar is 4-(CH$_3$)$_2$NC$_6$H$_4$, R is H], prepared from the compound of Preparation B15.

C20. 6-(4-Benzyloxyphenyl)-3-hexenyl bromide [V; Ar is 4-C$_6$H$_5$CH$_2$OC$_6$H$_4$, R is H], prepared from the compound of Preparation B17.

C21. 6-(3,4-Dibenzyloxyphenyl)-3-hexenyl bromide [V; Ar is 3,4-(C$_6$H$_5$CH$_2$O)$_2$C$_6$H$_3$, R is H], prepared from the compound of Preparation B18.

C22. 6-(4-Trifluoromethoxyphenyl)-3-hexenyl bromide [V; Ar is 4-F$_3$COC$_6$H$_4$, R is H], prepared from the compound of Preparation B19.

C23. 6-(1-Naphthyl)-3-hexenyl bromide [V; Ar is 1-naphthyl, R is H], prepared from the compound of Preparation B20.

C24. 6-(1-Naphthyl)hexyl bromide [Va; Ar is 1-naphthyl, R is H], b.p. 145°–146° C. (0.01 mm.), prepared by hydrogenation of the compound of Preparation C23.

C25. 6-(4-Fluorophenyl)-3-hexenyl bromide [V; Ar is 4-FC$_6$H$_4$, R is H], prepared from the compound of Preparation B21.

C26. 6-(4-Fluorophenyl)hexyl bromide [Va; Ar is 4-FC$_6$H$_4$, R is H], by hydrogenation of the compound of Preparation C25.

C27. 6-(4-Diethylaminophenyl)-3-hexenyl bromide [V; Ar is 4-(C$_2$H$_5$)$_2$NC$_6$H$_4$, R is H], prepared from compound of Preparation B22.

C28. 6-(4-Benzyloxy-3,5-dimethoxyphenyl)-3-hexenyl bromide [V; Ar is 3,5-(CH$_3$O)$_2$-4-C$_6$H$_5$CH$_2$OC$_6$H$_2$, R is H], prepared from compound of Preparation B23.

D. Arylalkenyl iodides (VI, IX) and arylalkyl iodides (VIa)

D1. 3-Ethyl-6-(3,4-methylenedioxyphenyl)-3-hexenyl iodide [VI; Ar is 3,4-methylenedioxyphenyl, R is C$_2$H$_5$].

A mixture of 23 g. of 3-ethyl-6-(3,4-methylenedioxyphenyl)-3-hexenyl bromide (Preparation C1) and 30 g. of powdered potassium iodide in 250 ml. of dimethylformamide was stirred for about sixteen hours. The reaction mixture was concentrated to remove the solvent and the residue partitioned between cyclohexane and water. The cyclohexane layer was separated; dried over anhydrous magnesium sulfate and evaporated to give 33.0 g. of 3-ethyl-6-(3,4-methylenedioxyphenyl)-3-hexenyl iodide as a light yellow oil.

D2. 6-(3,4-Methylenedioxyphenyl)-3-hexenyl iodide [VI; Ar is 3,4-methylenedioxyphenyl, R is H] was prepared from 12.9 g. of 6-(3,4-methylenedioxyphenyl)-3-hexenyl bromide (Preparation C2) and 7 g. of sodium iodide in 120 ml. of acetone, refluxed for three hours, affording 12.5 g. of product as an oil.

D3. 3-Methyl-6-(3,4-methylenedioxyphenyl)-3-hexenyl iodide [VI; Ar is 3,4-methylenedioxyphenyl, R is CH$_3$] was prepared from 19.0 g. of 3-methyl-6-(3,4-methylenedioxyphenyl)-3-hexenyl bromide (Preparation C3) and 10.5 g. of sodium iodide in 125 ml. of acetone, to give 21 g. of product as a yellow oil.

D4. 3-Ethyl-6-(3,4-dimethoxyphenyl)-3-hexenyl iodide [VI; Ar is 3,4-(CH$_3$O)$_2$C$_6$H$_3$, R is C$_2$H$_5$] was prepared from 13.8 g. of 3-ethyl-6-(3,4-dimethoxyphenyl)-3-hexenyl bromide (Preparation C4) and 9 g. of sodium iodide in 120 ml. of acetone, to give 15 g. of product as an oil.

D5. 6-(4-Methoxyphenyl)-3-hexenyl iodide [VI; Ar is 4-CH$_3$OC$_6$H$_4$, R is H] was prepared from 24 g. of 6-(4-methoxyphenyl)-3-hexenyl bromide (Preparation C5) and 14.75 g. of sodium iodide in 475 ml. of 2-butanone, to give 28.5 g. of product as an oil.

D6. 6-(4-Methoxyphenyl)hexyl iodide [VIa; Ar is 4-CH$_3$OC$_6$H$_4$, R is H] was prepared from 16.3 g. of 6-(4-methoxyphenyl)hexyl bromide (Preparation C11) and 9.93 g. of sodium iodide in 325 ml. of 2-butanone, to give 19.3 g. of product as a pale yellow oil.

D7. 6-Phenylhexyl iodide [VIa; Ar is C$_6$H$_5$, R is H] was prepared from 16 g. of 6-phenylhexyl bromide (Preparation C12) and 10.95 g. of sodium iodide in 325 ml. of 2-butanone, to give 19.1 g. of product as an oil.

D8. 6-(4-Chlorophenyl)hexyl iodide [VIa; Ar is 4-ClC$_6$H$_4$, R is H] was prepared from 17 g. of 6-(4-chlorophenyl)hexyl bromide (Preparation C13) and 10.2 g. of sodium iodide in 325 ml. of acetone, to give 21 g. of product as an oil.

D9. 6-(p-Tolyl)hexyl iodide [VIa; Ar is 4-CH$_3$C$_6$H$_4$, R is H] was prepared from 6-(p-tolyl)hexyl bromide (Preparation C14) and sodium iodide in acetone according to the procedure of Preparation D2 above.

D10. 3-Ethyl-6-(4-carbomethoxyphenyl)-3-hexenyl iodide [VI; Ar is 4-CH$_3$O$_2$CC$_6$H$_4$, R is C$_2$H$_5$] was prepared from 17.5 g. of 3-ethyl-6-(4-carbomethoxyphenyl)-3-hexenyl bromide (Preparation C9) and 17.5 g. of sodium iodide in 200 ml. of acetone, to give 14 g. of product as an oil.

D11. 3-Ethyl-6-(3,4-methylenedioxyphenyl)-3,5-hexadienyl iodide [IX; Ar is 3,4-methylenedioxyphenyl, R is C$_2$H$_5$] was prepared from 10 g. of 3-ethyl-6-(3,4-methylenedioxyphenyl)-3,5-hexadienyl bromide (Preparation C10) and 6 g. of sodium iodide in 120 ml. of acetone, to give 10.5 g. of product as an oil.

By similar procedures 3-isopropyl-6-(3,4-methylenedioxyphenyl)hexyl bromide, 3-butyl-6-(3,4-methylenedioxyphenyl)hexyl bromide, 6-(3,4-dichlorophenyl)hexyl bromide, 6-(2,4-dichlorophenyl)hexyl bromide, 6-(4-bromophenyl)hexyl bromide, 6-(4-fluorophenyl)hexyl bromide, 6-(4-benzoyloxyphenyl)-3-hexenyl bromide, 6-(4-trifluoromethoxyphenyl)hexyl bromide, or 6-(4-trifluoromethylphenyl)hexyl bromide can be caused to react with sodium iodide to give, respectively, 3-isopropyl-6-(3,4-methylenedioxyphenyl)hexyl iodide [VIa; Ar is 3,4-methylenedioxyphenyl, R is (CH$_3$)$_2$CH], 3-butyl-6-(3,4-methylenedioxyphenyl)hexyl iodide [VIa; Ar is 3,4-methylenedioxyphenyl, R is CH$_3$CH$_2$CH$_2$CH$_2$], 6-(3,4-dichlorophenyl)hexyl iodide [VIa; Ar is 3,4-Cl$_2$C$_6$H$_3$, R is H], 6-(2,4-dichlorophenyl)hexyl iodide [VIa; Ar is 2,4-Cl$_2$C$_6$H$_3$, R is H], 6-(4-bromophenyl)hexyl iodide [VIa; Ar is 4-BrC$_6$H$_4$, R is H], 6-(4-fluorophenyl)hexyl iodide [VIa; Ar is 4-FC$_6$H$_4$, R is H], 6-(4-benzoyloxyphenyl)-3-hexenyl bromide [VI; Ar is 4-C$_6$H$_5$COOC$_6$H$_4$, R is H], 6-(4-trifluoromethoxyphenyl)hexyl iodide [VIa; Ar is 4-

$F_3COC_6H_4$, R is H], or 6-(4-trifluoromethylphenyl)-hexyl iodide [VIa; Ar is 4-$F_3CC_6H_4$, R is H].

According to the procedures of Preparations D1–D11 using the appropriate starting materials, the following compounds were prepared:

D12. 6-(2,4-Dichlorophenyl)hexyl iodide [VIa; Ar is 2,4-$Cl_2$-$C_6H_3$, R is H], prepared from the compound of Preparation C16.

D13. 6-(4-Acetamidophenyl)-3-hexenyl iodide [VI; Ar is 4-$CH_3CONHC_6H_4$, R is H], prepared from the compound of Preparation C17.

D14. 8-(4-Methoxyphenyl)-3,7-octadienyl iodide, $ICH_2CH_2CH=CHCH_2CH_2CH=CHC_6H_4OCH_3$-4, prepared from the compound of Preparation C18.

D15. 6-(4-Dimethylaminophenyl)-3-hexenyl iodide [VI; Ar is 4-$(CH_3)_2NC_6H_4$, R is H], prepared from the compound of Preparation C19.

D16. 6-(4-Benzyloxyphenyl)-3-hexenyl iodide [VI; Ar is $C_6H_5CH_2OC_6H_4$, R is H], prepared from the compound of Preparation C20.

D17. 6-(3,4-Dibenzyloxyphenyl)-3-hexenyl iodide [VI; Ar is 3,4-$(C_6H_5CH_2O)_2C_6H_3$, R is H], prepared from the compound of Preparation C21.

D18. 6-(4-Trifluoromethoxyphenyl)-3-hexenyl iodide [VI; Ar is 4-$F_3COC_6H_4$, R is H], prepared from the compound of Preparation C22.

D19. 6-(1-Naphthyl)hexyl iodide [VIa; Ar is 1-naphthyl, R is H], prepared from the compound of Preparation C24.

D20. 6-(4-Fluorophenyl)hexyl iodide [VIa; Ar is 4-$FC_6H_4$, R is H], prepared from the compound of Preparation C26.

D21. 6-(4-Diethylaminophenyl)-3-hexenyl iodide [VI; Ar is 4-$(C_2H_5)_2NC_6H_4$, R is H], prepared from the compound of Preparation C27.

D22. 6-(4-Benzyloxy-3,5-dimethoxyphenyl)-3-hexenyl iodide [VI; Ar is 3,5-$(CH_3O)_2$-4-$C_6H_5CH_2OC_6H_2$, R is H], prepared from the compound of Preparation C28.

D23. 6-(p-Tolyl)-3-hexenyl iodide [VI; Ar is 4-$CH_3C_6H_4$, R is H], prepared from the compound of Preparation C8.

EXAMPLE 1

4-[3-Ethyl-6-(3,4-methylenedioxyphenyl)-3-hexenyl]-3,5-heptanedione [I; Ar is 3,4-methylenedioxyphenyl, R° is H, R' and R" are $CH_3CH_2CO$, Y is $C(C_2H_5)=CHCH_2CH_2$].

A solution of 15 g. of the lithium salt of 3,5-heptanedione (prepared as described in Example 3 below) in 100 ml. of tetramethylurea was stirred under nitrogen at room temperature, and 10 g. of 3-ethyl-6-(3,4-methylenedioxyphenyl)-3-hexenyl iodide (Preparation D1) was added. The reaction mixture was stirred for forty-eight hours, then concentrated to remove the solvent, and the residue slurried in ether and treated with excess glacial acetic acid. Water was added, the ether layer separated, washed with water and concentrated. The residue was distilled in a molecular still to remove volatile material at 110° C. (0.001 mm.), and the non-volatile residue was chromatographed on 10 g. of activated magnesium silicate in benzene solution and eluted with ethyl acetate to give 4-[3-ethyl-6-(3,4-methylenedioxyphenyl)-3-hexenyl]-3,5-heptanedione as a yellow oil.

The reaction was repeated starting with 38.4 g. of 3-ethyl-6-(3,4-methylenedioxyphenyl)-3-hexenyl iodide and the product was chromatographed twice on activated magnesium silicate. The second chromatogram was eluted with benzene to give 12.4 g. of 4-[3-ethyl-6-(3,4-methylenedioxyphenyl)-3-hexenyl]-3,5-heptanedione as a yellow oil.

Infrared (IR) (oil film) $\lambda_{82}^{max}$ 2.83w, 2.95w; 3.39. 3.92s (CH); 5.80s, 5.90s (C=O); 6.27ms, 6.23m, 6.65s, 6.71s, 6.94s (aromatic+CH).

4-[3-Ethyl-6-(3,4-methylenedioxyphenyl)-3-hexenyl]-3,5-heptanedione was found to have pesticidal activity when tested against yellow mealworm pupae (tenebrio) at a concentration of 0.1 microgram per insect, against dock beetle larvae at 1 microgram per insect, against yellow fever mosquito larvae at 15 ppm in water and against rhodnius prolixus nymph at 100 micrograms per insect.

EXAMPLE 2

3-[3-Ethyl-6-(3,4-methylenedioxyphenyl)-3-hexenyl]-2,4-pentanedione [I; Ar is 3,4-methylenedioxyphenyl, R° is H, R' and R" are $CH_3CO$, Y is $C(C_2H_5)=CHCH_2CH_2$].

A mixture of 10 g. of the lithium salt of 2,4-pentanedione (prepared by treatment of 2,4-pentanedione in ether with n-butyllithium by the procedure described in Example 3 below) and 10 g. of 3-ethyl-6-(3,4-methylenedioxyphenyl)-3-hexenyl iodide (Preparation D1) in 100 ml. of tetramethylurea was heated at 60° C. for forty-eight hours. The reaction mixture was filtered, the filtrate concentrated in vacuo to a volume of about 20 ml., then diluted with 200 ml. of water and extracted with ether. The ether solution was washed with water and saturated sodium chloride solution, and dried over anhydrous magnesium sulfate. The dried ether solution was concentrated to remove the solvent, and the residue was chromatographed on silica gel. The chromatograph column was eluted with pentane containing 20% benzene which removed unreacted iodide, and then eluted with benzene containing 20% ether, affording 2.4 g. of 3-[3-ethyl-6-(3,4-methylenedioxyphenyl)-3-hexenyl]-2,4-pentanedione as an amber oil.

Anal. Calcd. for $C_{20}H_{27}O_4$: C, 72.48; H, 8.21. Found: C, 72.34; H. 7.93.

IR (oil film)$\lambda_\mu^{max}$ 3.45mss+shldrs. (CH); 5.80 mss, 5.91s (C=O); 6.25m, 6.35m , 6.67mss, 6.73s, 6.96mss (arom+CH).

Nuclear Magnetic Resonance (NMR) [20% $CDCl_3$, internal tetramethylsilane (TMS)] δppm (Ratio) 6.63(3) (arom); 5.87(2) (O—$CH_2$—O); 5.08(1) (=CH); 3.53(1) [(O=C)$_2$CH]; 1.5–3.0(16) (aliphatic CH+ $COCH_3 \times 2$); 0.9(3) (Me triplet).

3-[3-Ethyl-6-(3,4-methylenedioxyphenyl)-3-hexenyl]-2,4-pentanedione was found to be pesticidal against yellow mealworm pupae (tenebrio) at a concentration of 100 micrograms per insect, against dock beetle larvae at 20 micrograms per insect, against cabbage looper larvae at 100 micrograms per insect and against rhodnius nymph at 30 micrograms per insect.

EXAMPLE 3

4-[3-Methyl-6-(3,4-methylenedioxyphenyl)-3-hexenyl]-3,5-heptanedione [I; Ar is 3,4-methylenedioxyphenyl, R° is H, R' and R" are $CH_3CH_2CO$, Y is $C(CH_3)=CHCH_2CH_2$].

To 40 g. of 3,5-heptanedione in 400 ml. of ether at 0° C. was added dropwise 19.9 g. of n-butyllithium in hexane solution. The mixture was warmed to 25° C., filtered and the solid product washed with ether and dried.

The resulting lithium salt of 3,5-heptanedione (20 g.), 20.6 g. of 3-methyl-6-(3,4-methylenedioxyphenyl)-3-hexenyl iodide (Preparation D3) and 200 ml. of dimethylformamide was stirred at 50° C. for twenty-four hours. Additional dimethylformamide (50 ml.) was then added and the mixture stirred at 60° C. for sixty-five hours. The solution was concentrated in vacuo and the residue triturated with ether several times. The ether solution was washed with water, dried over anhydrous magnesium sulfate and concentrated to give 18 g. of an oil which was chromatographed on 500 g. of silica gel, applied in pentane. The column was eluted with the pentane-benzene-ether solvent sequence. The desired product was brought out by benzene containing 3% ether, affording 10.2 g. of 4-[3-methyl-6-(3,4-methylenedioxyphenyl)-3-hexenyl]-3,5-heptanedione as a light yellow viscous oil.

Anal. Calcd. for $C_{21}H_{28}O_4$: C, 73.23; H, 8.19. Found: C, 73.44; H, 8.34.

IR (oil film) $\lambda_\mu^{max}$ 3.45mss+shldrs. (CH); 5.82mss, 5.92s (C=O); 6.26m, 6.35m, 6.68mss, 6.74s, 6.96mss+shldrs. (arom and CH).

NMR (20% $CDCl_3$, internal TMS) δ ppm (Ratio) 6.63(3) (arom CH); 5.87(2) (O—$CH_2$—O); 5.12(1) (=CH); 3.57(1) [(O=C)$_2$CH]; 1.4–2.8(15) (aliph. CH); 1.00(3) (Me triplet×2).

4-[3-Methyl-6-(3,4-methylenedioxyphenyl)-3-hexenyl]-3,5-heptanedione was found to have minimum inhibitory concentrations in vitro against rhino-2, equine rhino, parainfluenza and resp. sync. virus of 3, 6, 6 and 6 micrograms per milliliter, respectively.

4-[3-Methyl-6-(3,4-methylenedioxyphenyl)-3-hexenyl]-3,5-heptanedione was found to be pesticidal against yellow mealworm pupae (tenebrio) at a concentration of 3 micrograms per insect, against dock beetle larvae at 5 micrograms per insect and against yellow fever mosquito larvae at 6.6 ppm in water.

EXAMPLE 4

4-[3-Ethyl-6-(4-carbomethoxyphenyl)-3-hexenyl]-3,5-heptanedione [I; AR is 4-$CH_3O_2CC_6H_4$, R° is H, R' and R" are $CH_3CH_2CO$, Y is $C(C_2H_5)$=$CHCH_2CH_2$] was prepared from 14 g. of 3-ethyl-6-(4-carbomethoxyphenyl)-3-hexenyl iodide (Preparation D10) and 14 g. of the lithium salt of 3,5-heptanedione in 200 ml. of dimethylformamide according to the procedure described above in Example 2. The product was chromatographed on silica gel and eluted with the pentane-benzene-ether solvent series. Benzene containing 2% ether brought out the desired product, 2.6 g. of 4-[3-ethyl-6-(4-carbomethoxyphenyl)-3-hexenyl]-3,5-heptanedione as a yellow oil.

Anal. Calcd. for $C_{23}H_{32}O_4$: C, 74.16; H, 8.66. Found: C, 74.14; H, 8.53. C, 74.41; H, 8.69.

IR (oil film) $\lambda_\mu^{max}$ 3.44mss+shldrs. (CH); 5.77s, 5.90 shldr. (C=O); 6.24mms, 6.35m, 6.63w; 6.87mms, 6.98ms (arom+CH). NMR (20% $CDCl_3$, internal TMS) δ ppm (Ratio) 8.00(2), 7.25(2) (arom); 5.10(1+) (=CH); 3.88(3) (OMe); 3.61(1) [(O=C)$_2$CH], 0.7–3.0(22) (aliph. CH incl. Me triplets).

4-[3-Ethyl-6-(4-carbomethoxyphenyl)-3-hexenyl]-3,5-heptanedione was found to have a minimum inhibitory concentration in vitro of 25 micrograms per milliliter against equine rhino virus.

4-[3-Ethyl-6-(4-carbomethoxyphenyl)-3-hexenyl]-3,5-heptanedione was found to be pesticidal against dock beetle larvae at a concentration of 1 microgram per insect.

EXAMPLE 5

4-[6-(4-Acetamidophenyl)-3-hexenyl]-3,5-heptanedione [I; Ar is 4-$CH_3CONHC_6H_4$, R° is H, R' and R" are $CH_3CH_2CO$, Y is CH=$CHCH_2CH_2$] was prepared from the compound of Preparation D13 and the lithium salt of 3,5-heptanedione, and obtained as a viscous amber oil, b.p. 215°–220° C. (0.02 mm.).

Anal. Calcd. for $C_{21}H_{29}NO_3$: C, 73.44; H, 8.51; N, 4.08. Found: C, 72.95; H, 8.45; N, 4.43.

IR (oil film) $\lambda_\mu^{max}$ 3.12ms+shldrs. (NH); 3.50ms+shldrs. (CH); 5.85, 5.97, 6.06s (C=O, N—C=O); 6.30s, 6.57s, 6.65s, 6.93, 7.00 shldr. (arom+CH).

4-[6-(4-Acetamidophenyl)-3-hexenyl]-3,5-heptanedione was active against equine rhino virus in vitro at 12 micrograms per milliliter.

EXAMPLE 6

4-[6-(4-Dimethylaminophenyl)-3-hexenyl]-3,5-heptanedione [I; Ar is 4-$(CH_3)_2NC_6H_4$, R° is H, R' and R" are $CH_3CH_2CO$, Y is CH=$CHCH_2CH_2$] was prepared from the compound of Preparation D15 and the lithium salt of 3,5-heptanedione, and obtained as pale yellow oil, b.p. 155°–159° C. (0.003 mm.).

Anal. Calcd. for $C_{21}H_{31}NO_2$: C, 76.55; H, 9.48; N, 4.25. Found: C, 77.04; H, 9.63; N, 4.61.

IR (oil film) $\lambda_\mu^{max}$ 3.43s+shldrs., 3.53ms (CH); 5.79, 5.89s (C=O); 6.26ms, 6.32 shldr., 6.39m, 6.57s, 6.76m, 6.90ms (arom+CH).

4-[6-(4-Dimethylaminophenyl)-3-hexenyl]-3,5-heptanedione was active against equine rhino virus in vitro at 3 micrograms per milliliter. It was also active against para-influenza virus and several strains of human rhino virus at 1.5–7 micrograms per milliliter.

EXAMPLE 7

4-[6-(4-Benzyloxyphenyl)-3-hexenyl]-3,5-heptanedione [I; Ar is 4-$C_6H_5CH_2OC_6H_4$, R° is H, R' and R" are $CH_3CH_2CO$, Y is CH=$CHCH_2CH_2$] was prepared from the compound of Preparation D16 and the lithium salt of 3,5-heptanedione, and obtained as a colorless solid, m.p. 36°–37° C. when recrystallized from ether.

Anal. Calcd. for $C_{26}H_{32}O_3$: C, 79.56; H, 8.22. Found: C, 79.51; H, 8.31.

4-[6-(4-Benzyloxyphenyl)-3-hexenyl]-3,5-heptanedione was active against equine rhino virus in vitro at 3 micrograms per milliliter. It was also active against two strains of human rhino virus at 0.3 micrograms per milliliter.

EXAMPLE 8

4-[6-(4-Hydroxy-3,5-dimethoxyphenyl)hexyl]-3,5-heptanedione [I; Ar is 3,5-$(CH_3O)_2$-4-$HOC_6H_2$, R° is H, R' and R" are $CH_3CH_2CO$, Y is $CH_2CH_2CH_2CH_2$], yellow oil, was prepared from the compound of Preparation D22 and the lithium salt of 3,5-heptanedione, followed by catalytic hydrogenation of the resulting 4-[6-(4-benzyloxy-3,5-dimethoxyphenyl)-3-hexenyl]-3,5-heptanedione (light yellow oil).

EXAMPLE 9

(a) Diethyl [6-(4-benzyloxyphenyl)-3-hexenyl]malonate.

A mixture of 205.8 g. of 6-(4-benzyloxyphenyl)-3-hexenyl iodide (Preparation D16) and 171 g. of the lithium salt of diethyl malonate in 1650 ml. of dimethylformamide was heated at 50°-60° C. for 16 hours. The reaction mixture was concentrated to dryness, the residue partitioned between water and ether, and the ether layer washed with sodium chloride solution, dried and concentrated to give 226 g. of diethyl [6-(4-benzyloxyphenyl)-3-hexenyl]malonate, used in the next reaction without further purification.

(b) 8-(4-Benzyloxyphenyl)-5-octenoic acid [4-$C_6H_5CH_2OC_6H_4CH_2CH_2$—CH=$CHCH_2CH_2CH_2COOH$].

A mixture of 222 g. of diethyl [6-(4-benzyloxyphenyl)-3-hexenyl]malonate, 286 g. of 85% potassium hydroxide and 510 ml. of water was refluxed for two hours. The reaction mixture was cooled, acidified with hydrochloric acid and extracted with chloroform. The chloroform extracts were dried and concentrated, and the residue was dissolved in 600 ml. of xylene and heated at reflux for about 16 hours. The solution was cooled, the solvent removed in vacuo, and the residue crystallized from cyclohexanepentane to give 110 g. of 8-(4-benzyloxyphenyl)-5-octenoic acid, m.p. 63°-65° C.

(c) 8-(4-Benzyloxyphenyl)-5-octenol [4-$C_6H_5CH_2OC_6H_4CH_2CH_2CH$=CH—$CH_2CH_2Ch_2CH_2OH$].

A solution of 110 g. of 8-(4-benzyloxyphenyl)-5-octenoic acid in 400 ml. of tetrahydrofuran was added dropwise to a slurry of 13.4 g. of lithium aluminum hydride in 630 ml. of tetrahydrofuran at such a rate as to maintain reflux. The reaction mixture was heated at reflux for four hours, then cooled, and 26.5 ml. of tetrahydrofuran and 26.5 ml. of water were added. The solvents were removed in vacuo and the residue crystallized from cyclohexane to give 98 g. of 8-(4-benzyloxyphenyl)-5-octenol, m.p. 65°-67° C.

(d) 8-(4-Benzyloxyphenyl)-5-octenyl p-toluenesulfonate.

8-(4-Benzyloxyphenyl)-5-octenol (24 g.) was added in portions over a 15 minute period to a solution of 19.5 g. of p-toluenesulfonyl chloride in 600 ml. of dry pyridine at −10° C. The reaction mixture was stirred for one hour at −10° C., then poured into ice-water and stirred for 20 minutes. The mixture was extracted with chloroform, and the latter washed with aqueous hydrochloric acid, aqueous sodium hydroxide, dried and concentrated. The resulting 8-(4-benzyloxyphenyl)-5-octenyl p-toluenesulfonate was used directly in the next reaction without further purification.

(e) 8-(4-Benzyloxyphenyl)-5-octenyl iodide [4-$C_6H_5CH_2OC_6H_4CH_2CH_2$—CH=$CHCH_2CH_2CH_2CH_2I$].

A mixture of 33.2 g. of 8-(4-benzyloxyphenyl)-5-octenyl p-toluenesulfonate, 12.6 g. of sodium iodide and 370 ml. of 2-butanone was heated at reflux for four hours, then filtered and concentrated to remove the solvent. The residue was partitioned between ether and water, and the ether solution was washed with aqueous sodium thiosulfate, dried and concentrated to give 26.4 g. of 8-(4-benzyloxyphenyl)-5-octenyl iodide.

(f) 4-[8-(4-Benzyloxyphenyl)-5-octenyl]-3,5-heptanedione [I; Ar is 4-$C_6H_5CH_2OC_6H_4$, R° is H, R' and R" are $CH_3CH_2CO$, Y is $CH_2CH_2CH=CHCH_2CH_2$] was prepared from 8-(4-benzyloxyphenyl)-5-octenyl iodide and the lithium salt of 3,5-heptanedione, and obtained as an oil used directly in the hydrogenation procedure below.

(g) 4-[8-(4-Hydroxyphenyl)octyl]-3,5-heptanedione [I; Ar is 4-$C_6H_5CH_2C_6H_4$, R° is H, R' and R" are $CH_3CH_2CO$, Y is $CH_2CH_2CH_2CH_2CH_2CH_2$] was prepared by hydrogenating 4-[8-(4-benzyloxyphenyl)-5-octenyl]-3,5-heptanedione in the presence of palladium-on-carbon catalyst, and obtained as colorless crystals, m.p. 164°-165° C.

Anal. Calcd. for $C_{21}H_{32}O_3$: C, 75.86; H, 9.70. Found: C, 75.91; H, 9.78.

4-[8-(4-Hydroxyphenyl)octyl]-3,5-heptanedione was active against equine rhino virus in vitro at 3 micrograms per milliliter, and against para-influenza virus at 6 and two strains of human rhino virus at 0.3 and 1.5 micrograms per milliliter.

EXAMPLE 10

4-{6-[4-(Methoxybenzoyloxy)phenyl]hexyl}-3,5-heptanedione [I; Ar is 4-$CH_3OC_6H_4$-$COOC_6H_4$, R° is H, R' and R" are $CH_3CH_2CO$, Y is $CH_2CH_2CH_2CH_2$].

To a solution of 6.8 g. of 4-[6-(4-hydroxyphenyl)hexyl]-3,5-heptanedione in 30 ml. of dry pyridine was added 7.65 g. of p-anisoyl chloride over a period of 10 minutes. The reaction mixture was stirred overnight at room temperature and then poured into water. The mixture was extracted with ether, and the ether extracts were washed successively with 2 N hydrochloric acid, water, 5% aqueous sodium bicarbonate, and water, then dried over anhydrous magnesium sulfate and concentrated. The residue was chromatographed on 270 g. of activated magnesium silicate and eluted with the pentane-benzene-ether solvent series. Benzene-ether 8:2 brought out 4.2 g. of 4-{6-[4-(methoxybenzoyloxy)phenyl]hexyl}-3,5-heptanedione as a light yellow solid.

Anal. Calcd. for $C_{27}H_{34}O_5$: C, 73.94; H, 7.81. Found: C, 73.53; H, 7.60.

4-{6-[4-(Methoxybenzoyloxy)phenyl]hexyl}-3,5-heptanedione was found to be active in vivo upon intragastral or subcutaneous administration at 200 mg/kg to mice infected with Jap 170 influenza strain, whereby 60% of the medicated mice survived.

EXAMPLE 11

4-{6-[4-(Methylbenzoyloxy)phenyl]hexyl}-3,5-heptanedione [I; Ar is 4-$CH_3C_6H_4COOC_6H_4$, R° is H, R' and R" are $CH_3CH_2CO$, Y is $CH_2CH_2CH_2CH_2$] was prepared from 4-[6-(4-hydroxyphenyl)hexyl]-3,5-heptanedione and p-toluyl chloride according to the procedure of Example 10, and was obtained in the form of off-white crystals, m.p. 72°-75° C.

Anal. Calcd. for $C_{27}H_{34}O_4$: C, 76.74; H, 8.11. Found: C, 76.89; H, 8.11.

By procedures analogous to that of Example 37, using the appropriate acid chloride, the following esters of 4-[6-(4-hydroxyphenyl)hexyl]-3,5-heptanedione were obtained, all in the form of light yellow oils: 3-methoxybenzoate; 3-methylbenzoate; 3,5-dimethoxybenzoate; and 2-methylbenzoate.

EXAMPLE 12

4-[6-(4-Hydroxyphenyl)-hexyl]-3,5-heptanedione 4-morpholinobutanoate [I; Ar is 4-$O(CH_2)_4N(CH_2)_3COOC_6H_4$, R° is H, R' and R" are $CH_3CH_2CO$, Y is $CH_2CH_2CH_2CH_2$].

A suspension of 5 g. of 4-[6-(4-hydroxyphenyl)hexyl]-3,5-heptanedione, 3.45 g. of 4-morpholinobutyric acid hydrochloride and 3.74 g. of dicyclohexylcarbodiimide (DCC) in 50 ml. of methylene dichloride was stirred at room temperature for two days. The solid dicyclohexyl urea was removed by filtration and washed with methylene dichloride. The combined washings and filtrate was concentrated to dryness and the residue triturated with ether to induce crystallization of the product. The latter was collected and dried to give 7.45 g. of 4-[6-(4-hydroxyphenyl)hexyl]-3,5-heptanedione 4-morpholinobutanoate in the form of its hydrochloride salt, light tan solid, m.p. 57°–59° C.

Anal. Calcd. for $C_{27}H_{41}NO_2 \cdot HCl$: C, 65.37; H, 8.53; N, 2.82; Cl, 7.15. Found: C, 65.11; H, 8.44; N, 3.08; Cl, 7.37.

By replacing the 4-morpholinobutyric acid hydrochloride in the foregoing preparation by a molar equivalent amount of 4-diethylaminobutyric acid hydrochloride there can be prepared 4-[6-(4-hydroxyphenyl)hexyl]-3,5-heptanedione 4-diethylaminobutanoate [I; Ar is $4-(C_2H_5)_2N(CH_2)_3COOC_6H_4$, R° is H, R' and R" are $CH_3CH_2CO$, Y is $CH_2CH_2CH_2CH_2$].

The glycinate ester of 4-[6-(4-hydroxyphenyl)hexyl]-3,5-heptanedione [I; Ar is $4-NH_2CH_2COOC_6H_4$, R° is H, R' and R" are $CH_3CH_2CO$, Y is $CH_2CH_2CH_2CH_2$] can be prepared by reacting the phenolic compound with carbobenzoxyglycine to form the carbobenzoxyglycine ester, and removing the carbobenzoxy group with acetic acid saturated with hydrogen bromide.

4-[6-(4-Hydroxyphenyl)hexyl]-3,5-heptanedione can be caused to react with acetic anhydride, propionic anhydride, caproyl chloride, succinic anhydride, β-cyclopentylpropionyl chloride, p-nitrobenzoyl chloride, 3,4,5-trimethoxybenzoyl chloride, phenylacetyl chloride or cinnamoyl chloride to give, respectively, the acetate, propionate, caproate, hemisuccinate, β-cyclopentylpropionate, p-nitrobenzoate, 3,4,5-trimethoxybenzoate, phenylacetate or cinnamate ester of 4-[6-(4-hydroxyphenyl)hexyl]-3,5-heptanedione.

EXAMPLE 13

(a) 4-[6-(3-Benzyloxyphenyl)-3-hexenyl]-3,5-heptanedione [I; Ar is $3-C_6H_5CH_2OC_6H_4$, R° is H, R' and R" are $CH_3CH_2CO$, Y is $CH=CHCH_2CH_2$] was prepared according to Reaction Sequence A starting with m-benzyloxybenzaldehyde and cyclopropyl methyl ketone.

(b) 4-[6-(3-Hydroxyphenyl)hexyl]-3,5-heptanedione [I; Ar is $3-HOC_6H_4$, R° is H, R' and R" are $CH_3CH_2CO$, Y is $CH_2CH_2CH_2CH_2$] was prepared by catalytic hydrogenation of 4-[6-(3-benzyloxyphenyl)-3-hexenyl]-3,5-heptanedione with palladium-on-carbon. The product was chromatographed on silica gel and eluted with ethyl acetate-chloroform 1:9 to give 4-[6-(3-hydroxyphenyl)hexyl]-3,5-heptanedione as a colorless oil.

Anal. Calcd. for $C_{19}H_{28}O_3$: C, 74.96; H, 9.27. Found: C, 74.62; H, 9.34.

EXAMPLE 14

(a) 3-[6-(4-Benzyloxyphenyl)-3-hexenyl]-2,4-pentanedione [I; Ar is $3-C_6H_5CH_2OC_6H_4$, R° is H, R' and R" are $CH_3CO$, Y is $CH=CHCH_2CH_2$] was prepared by reacting 6-(4-benzyloxyphenyl)-3-hexenyl iodide (Preparation D16) with lithium pentane-2,4-dione. The product was chromatographed on activated magnesium silicate and eluted with benzene.

(b) 3-[6-(4-Hydroxyphenyl)hexyl]-2,4-pentanedione [I; Ar is $3-HOC_6H_4$, R° is H, R' and R" are $CH_3CO$, Y is $CH_2CH_2CH_2CH_2$] was prepared by catalytic hydrogenation of 3-[6-(4-benzyloxyphenyl)-3-hexenyl]-2,4-pentanedione and had the m.p. 68°–69° C.

Anal. Calcd. for $C_{17}H_{24}O_3$: C, 73.88; H, 8.75. Found: C, 74.08; H, 8.80.

EXAMPLE 15

4-[6-(4-Hydroxyphenyl)hexyl-3,5-heptanedione 3,4,5-trimethoxybenzoate [I; Ar is $3,4,5-(CH_3O)_3C_6H_2COOC_6H_4$, R° is H, R' and R" are $CH_3CH_2CO$, Y is $CH_2CH_2CH_2CH_2$].

A mixture of 6 g. of 4-[6-(4-hydroxyphenyl)hexyl]-3,5-heptanedione and 55 ml. of pyridine was cooled to 0° C. and 9 g. of 3,4,5-trimethoxybenzoyl chloride was added. The reaction mixture was stirred for 30 minutes at 0° C. and at room temperature overnight. The product was isolated, chromatographed on activated magnesium silicate and eluted with pentane-benzene to give 9 g. of 4-[6-(4-hydroxyphenyl)hexyl]-3,5-heptanedione 3,4,5-trimethoxybenzoate as a yellow viscous oil.

Anal. Calcd. for $C_{29}H_{38}O_7$: C, 69.85; H, 7.82. Found: C, 69.16; H, 7.70.

4-[6-(4-Hydroxyphenyl)hexyl]-3,5-heptanedione 3,4,5-trimethoxybenzoate was active against equine rhino virus in vitro at 6 micrograms per milliliter.

EXAMPLE 16

4-[6-(4-Hydroxyphenyl)hexyl]-3,5-heptanedione acetate [I; Ar is $4-(CH_3COO)C_6H_4$, R° is H, R' and R" are $CH_3CH_2CO$, Y is $CH_2CH_2CH_2CH_2$] was prepared by acetylation of 6-(4-hydroxyphenyl)hexyl iodide with acetic anhydride and reaction of the resulting 6-(4-acetoxyphenyl)hexyl iodide with the lithium salt of 3,5-heptanedione, and was obtained in the form of an amber liquid.

Anal. Calcd. for $C_{21}H_{30}O_4$: C, 72.79; H, 8.73. Found: C, 72.85; H, 8.81.

EXAMPLE 17

4-[6-(4-Aminosulfonylphenyl)-3-hexenyl]-3,5-heptanedione [I; Ar is $4-H_2NSO_2C_6H_4$, R° is H, R' and R" are $CH_3CH_2CO$, Y is $CH=CHCH_2CH_2$] was prepared according to the reaction sequences described above starting with p-aminosulfonylbenzaldehyde and cyclopropyl methyl ketone, via the following intermediates:

2-(4-Aminosulfonylphenyl)vinyl cyclopropyl ketone, m.p. 173° C.;

2-(4-Aminosulfonylphenyl)ethyl cyclopropyl ketone, m.p. 141°–142° C.;

2-(4-Aminosulfonylphenyl)ethyl cyclopropyl carbinol, m.p. 92°–95° C.;

4-[6-(4-Aminosulfonylphenyl)-3-hexenyl] bromide;

4-[6-(4-Aminosulfonylphenyl)-3-hexenyl] iodide.

4-[6-(4-Aminosulfonylphenyl)-3-hexenyl]-3,5-heptanedione was obtained in the form of a light yellow solid.

Anal. Calcd. for $C_{19}H_{27}NO_4S$: C, 62.43; H, 7.45; N, 3.83. Found: C, 61.18; H, 7.15; N, 4.02.

EXAMPLE 18

4-{6-[4-(2-Ethoxyethoxy)phenyl]hexyl}-3,5-heptanedione [I; Ar is $4-(C_2H_5OCH_2CH_2O)C_6H_4$, R° is H, R' and R" are $CH_3CH_2CO$, Y is $CH_2CH_2CH_2CH_2$].

A mixture of 3.9 g. of 4-[6-(4-hydroxyphenyl)hexyl]-3,5-heptanedione, 12 g. of 2-bromoethyl ethyl ether, 4 g. of potassium carbonate and 1 g. of potassium iodide in 40 ml. of acetone was heated at reflux for 48 hours and then allowed to stand at room temperature for three days. The reaction mixture was then filtered and concentrated to remove the solvent. The residue was distilled at 200°–205° C. (0.001 mm.) to give 4-{6-[4-(2- ethoxyethoxy)phenyl]hexyl}-3,5-heptanedione as a light yellow oil.

Anal. Calcd. for $C_{23}H_{36}O_4$: C, 73.37; H, 9.64. Found: C, 73.03; H, 9.70.

4-{6-[4-(2-Ethoxyethoxy)phenyl]hexyl}-3,5-heptanedione was active against herpes 2 virus in vitro at 6 micrograms per milliliter.

I claim:

1. A compound of the formula

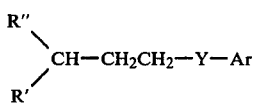

wherein
Y is selected from the group consisting of

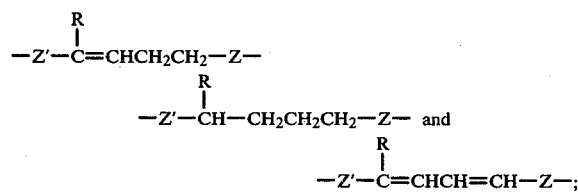

R' and R" are lower-alkanoyl of 2 to 6 carbon atoms;
R is hydrogen or lower-alkyl of 1 to 4 carbon atoms;
Z is a single bond, vinylene only when the remainder of Y is unsaturated, or ethylene only when Y is saturated;
Z' is a single bond, methylene or ethylene; and
Ar is phenyl substituted by a single substituent selected from the group consisting of carbo-lower-alkoxy of 2 to 4 carbon atoms, alkanoylamino of 1 to 4 carbon atoms, acyloxy of 1 to 10 carbon atoms, dialkylamino where alkyl has from 1 to 4 carbon atoms, and aminosulfonyl.

2. A compound according to claim 1 wherein Ar is phenyl substituted by carbo-lower-alkoxy of 2 to 4 carbon atoms.

3. 4-[3-Ethyl-6-(4-carbomethoxyphenyl)-3-hexenyl]-3,5-heptanedione, according to claim 2.

4. A composition for combatting viruses which comprises an antivirally effective amount of at least one compound according to claim 2 in admixture with a suitable carrier or diluent.

5. A method for combatting viruses which comprises contacting the locus of said viruses with a composition containing an antivirally effective amount of at least one compound according to claim 2 in admixture with a suitable carrier or diluent.

6. A compound according to claim 1 wherein Ar is phenyl substituted by alkanoylamino of 1 to 4 carbon atoms.

7. 4-[6-(4-Acetamidophenyl)-3-hexenyl]-3,5-heptanedione, according to claim 6.

8. A composition of combatting viruses which comprises an antivirally effective amount of at least one compound according to claim 6 in admixture with a suitable carrier or diluent.

9. A method for combatting viruses which comprises contacting the locus of said viruses with a composition containing an antivirally effective amount of at least one compound according to claim 6 in admixture with a suitable carrier or diluent.

10. A compound according to claim 1 wherein Ar is phenyl substituted by acyloxy of 1 to 10 carbon atoms.

11. A compound according to claim 10 wherein Ar is benzoyloxyphenyl, optionally substituted on the benzoyl group by from one to three lower-alkyl or lower-alkoxy groups of from one to four carbon atoms.

12. A 4-{6-[4-(4-Methoxybenzoyloxy)phenyl]hexyl}-3,5-heptanedione, according to claim 11.

13. 4-{6-[4-(4-Methoxybenzoyloxy)phenyl]hexyl}-3,5-heptanedione, according to claim 11.

14. 4-[6-(4-Hydroxyphenyl)hexyl]-3,5-heptanedione 3,4,5-trimethoxybenzoate, according to claim 11.

15. A compound according to claim 10 wherein Ar is amino-lower-alkanoyloxyphenyl.

16. 4-[6-(4-Hydroxyphenyl)hexyl]-3,5-heptanedione 4-morpholinobutanoate, according to claim 15.

17. A compound according to claim 10 wherein Ar is lower-alkanoyloxyphenyl wherein lower-alkanoyl has from one to four carbon atoms.

18. 4-[6-(4-Hydroxyphenyl)hexyl]-3,5-heptanedione acetate, according to claim 17.

19. A composition for combatting viruses which comprises an antivirally effective amount of at least one compound according to claim 10 in admixture with a suitable carrier or diluent.

20. A method for combatting viruses which comprises contacting the locus of said viruses with a composition containing an antivirally effective amount of at least one compound according to claim 10 in admixture with a suitable carrier or diluent.

21. A compound according to claim 1 wherein Ar is phenyl substituted by dialkylamino where alkyl has from 1 to 4 carbon atoms.

22. 4-[6-(4-Dimethylaminophenyl)-3-hexenyl]-3,5-heptanedione, according to claim 21.

23. A composition for combatting viruses which comprises an antivirally effective amount of at least one compound according to claim 21 in admixture with a suitable carrier or diluent.

24. A method for combatting viruses which comprises contacting the locus of said viruses with a composition containing an antivirally effective amount of at least one compound according to claim 21 in admixture with a suitable carrier or diluent.

25. A compound according to claim 1 wherein Ar is aminosulfonylphenyl.

26. 4-[6-(4-Aminosulfonylphenyl)-3-hexenyl]-3,5-heptanedione, according to claim 25.

* * * * *

UNITED STATES PATENT AND TRADEMARK OFFICE
CERTIFICATE OF CORRECTION

PATENT NO. : 4,275,201
DATED : June 23, 1981
INVENTOR(S) : Joseph C. Collins

It is certified that error appears in the above-identified patent and that said Letters Patent are hereby corrected as shown below:

Column 5, line 53, "can be" should read --can then be--; line 67, "aidic" should read --acidic--; line 68, "alkylaion" should read --alkylation--.

Column 6, line 19, "lace" should read --place--; line 21, "ryl" should read --aryl--; line 22, "y" should read --by--; line 23, "hydrox" should read --hydroxy--; line 37, "monocarboxylic" should read --monocarbocyclic--.

Column 28, line 1, Claim 8, "of combatting" should read --for combatting--; line 16, Claim 12, delete "A" at beginning of claim; line 18, Claim 13, "Methoxy" should read --Methyl--.

Signed and Sealed this

Twenty-third Day of March 1982

[SEAL]

Attest:

GERALD J. MOSSINGHOFF

*Attesting Officer*     *Commissioner of Patents and Trademarks*